(12) United States Patent
Hwang et al.

(10) Patent No.: US 9,216,117 B2
(45) Date of Patent: Dec. 22, 2015

(54) ABSORBENT ARTICLE WITH POINT FUSION BONDING

(75) Inventors: EoYeon Hwang, Yongin-si (KR); JinYoung Jung, Hwasung-Si (KR); WonYoung Lee, Yongin (KR); JinHee Lee, Anyang (KR); Richard Norris Dodge, II, Appleton, WI (US); David Arthur Fell, Neenah, WI (US); Eric Donald Johnson, Larsen, WI (US); Debra Jean McDowall, Medellin (CO); Robert Lee Popp, Greenville, WI (US); Allyson Marie Sagel, Greenville, WI (US); Lawrence Howell Sawyer, Medellin (CO); Daniel Robert Schlinz, Greenville, WI (US); Michael W. Veith, Fremont, WI (US); Kendell Jean Williams, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 707 days.

(21) Appl. No.: 13/435,321

(22) Filed: Mar. 30, 2012

(65) Prior Publication Data
US 2013/0261579 A1    Oct. 3, 2013

(51) Int. Cl.
| A61F 13/15 | (2006.01) |
| A61F 13/20 | (2006.01) |
| A61F 13/511 | (2006.01) |
| A61L 15/58 | (2006.01) |
| A61F 13/537 | (2006.01) |

(52) U.S. Cl.
CPC ........... *A61F 13/5116* (2013.01); *A61F 13/537* (2013.01); *A61F 13/53708* (2013.01); *A61F 13/53713* (2013.01); *A61F 13/53717* (2013.01); *A61F 13/53747* (2013.01); *A61F 13/53756* (2013.01); *A61L 15/58* (2013.01)

(58) Field of Classification Search
USPC .................... 604/367, 378, 379–380, 385.01, 604/385.101
See application file for complete search history.

(56) References Cited

U.S. PATENT DOCUMENTS

| 3,924,626 | A |   | 12/1975 | Lee et al. |
| 4,397,644 | A |   | 8/1983  | Matthews et al. |
| 4,573,986 | A |   | 3/1986  | Minetola et al. |
| 4,646,510 | A |   | 3/1987  | McIntyre |
| 4,775,579 | A | * | 10/1988 | Hagy et al. .................... 442/329 |
| 4,798,603 | A |   | 1/1989  | Meyer et al. |
| 4,950,264 | A |   | 8/1990  | Osborn, III |
| 5,009,653 | A |   | 4/1991  | Osborn, III |

(Continued)

FOREIGN PATENT DOCUMENTS

| EP | 0 295 957 A1 | 12/1988 |
| EP | 0 456 281 A2 | 11/1991 |

(Continued)

OTHER PUBLICATIONS

Co-pending U.S. Appl. No. 13/435,248, filed Mar. 30, 2012, by Hwang et al. for "Absorbent Article."

(Continued)

*Primary Examiner* — Michele M Kidwell
(74) *Attorney, Agent, or Firm* — Kimberly-Clark Worldwide, Inc.

(57) ABSTRACT

An absorbent article having improved handling of liquid and improved intake and retention of liquid loadings during use. The absorbent article can minimize the amount of moisture in contact with a wearer's skin and can provide a feeling of softness on the skin of the wearer.

24 Claims, 22 Drawing Sheets

(56) References Cited

U.S. PATENT DOCUMENTS

| | | | |
|---|---|---|---|
| 5,019,062 A | 5/1991 | Ryan et al. | |
| 5,137,600 A * | 8/1992 | Barnes et al. | 162/115 |
| 5,192,606 A | 3/1993 | Proxmire et al. | |
| 5,284,703 A | 2/1994 | Everhart et al. | |
| 5,304,161 A | 4/1994 | Noel et al. | |
| 5,383,869 A | 1/1995 | Osborn, III | |
| 5,423,787 A | 6/1995 | Kjellberg | |
| 5,439,458 A | 8/1995 | Noel et al. | |
| 5,458,952 A | 10/1995 | Wagner et al. | |
| 5,466,232 A | 11/1995 | Cadieux et al. | |
| 5,509,915 A | 4/1996 | Hanson et al. | |
| 5,520,673 A | 5/1996 | Yarbrough et al. | |
| 5,591,149 A | 1/1997 | Cree et al. | |
| 5,611,790 A * | 3/1997 | Osborn et al. | 604/391 |
| 5,613,960 A | 3/1997 | Mizutani | |
| 5,658,268 A | 8/1997 | Johns et al. | |
| 5,746,729 A | 5/1998 | Wada et al. | |
| 5,792,129 A | 8/1998 | Johansson et al. | |
| 5,797,894 A | 8/1998 | Cadieux et al. | |
| 5,801,107 A | 9/1998 | Everhart et al. | |
| 5,843,064 A | 12/1998 | Koczab | |
| 5,846,230 A | 12/1998 | Osborn, III et al. | |
| 5,885,623 A | 3/1999 | Edvardsson et al. | |
| 5,954,705 A | 9/1999 | Sawaki et al. | |
| 6,068,620 A | 5/2000 | Chmielewski | |
| 6,231,555 B1 | 5/2001 | Lynard et al. | |
| 6,312,416 B1 | 11/2001 | Brisebois et al. | |
| 6,441,266 B1 | 8/2002 | Dyer et al. | |
| 6,452,062 B1 | 9/2002 | Koczab | |
| 6,462,253 B1 | 10/2002 | Magnusson et al. | |
| 7,102,054 B1 | 9/2006 | Cree et al. | |
| 2001/0044610 A1 | 11/2001 | Kim et al. | |
| 2002/0004654 A1 | 1/2002 | Daniels et al. | |
| 2002/0019614 A1 * | 2/2002 | Woon et al. | 604/358 |
| 2002/0034914 A1 * | 3/2002 | De Leon et al. | 442/384 |
| 2003/0143376 A1 | 7/2003 | Toyoshima et al. | |
| 2005/0027277 A1 | 2/2005 | Mizutani et al. | |
| 2006/0229579 A1 | 10/2006 | Wahlstrom et al. | |
| 2007/0044903 A1 | 3/2007 | Wisneski et al. | |
| 2007/0049892 A1 | 3/2007 | Lord et al. | |
| 2009/0131896 A1 | 5/2009 | Ebitsuka et al. | |
| 2011/0238026 A1 | 9/2011 | Zhang et al. | |
| 2013/0261578 A1 * | 10/2013 | Hwang et al. | 604/365 |
| 2013/0261582 A1 * | 10/2013 | Hwang et al. | 604/378 |
| 2013/0261583 A1 * | 10/2013 | Hwang et al. | 604/378 |
| 2014/0121621 A1 * | 5/2014 | Kirby | A61F 13/5126 604/374 |
| 2014/0121624 A1 * | 5/2014 | Kirby | A61F 13/51108 604/383 |

FOREIGN PATENT DOCUMENTS

| | | | |
|---|---|---|---|
| EP | 0 685 214 A2 | 12/1995 | |
| EP | 0 847 263 B1 * | 1/2002 | A61F 13/15 |
| EP | 1 362 568 A2 | 11/2003 | |
| GB | 2 319 730 A | 6/1998 | |
| GB | 2 354 449 A | 3/2001 | |
| WO | WO 93/11725 A1 | 6/1993 | |
| WO | WO 98/27904 A1 | 7/1998 | |
| WO | WO 99/58092 A1 | 11/1999 | |
| WO | WO 00/32145 A1 | 6/2000 | |
| WO | WO 00/32146 A1 | 6/2000 | |
| WO | WO 00/32147 A1 | 6/2000 | |
| WO | WO 01/17475 A1 | 3/2001 | |

OTHER PUBLICATIONS

Co-pending U.S. Appl. No. 13/435,285, filed Mar. 30, 2012, by Hwang et al. for "Absorbent Article."

Co-pending U.S. Appl. No. 13/435,357, filed Mar. 30, 2012, by Hwang et al. for "Absorbent Article."

* cited by examiner

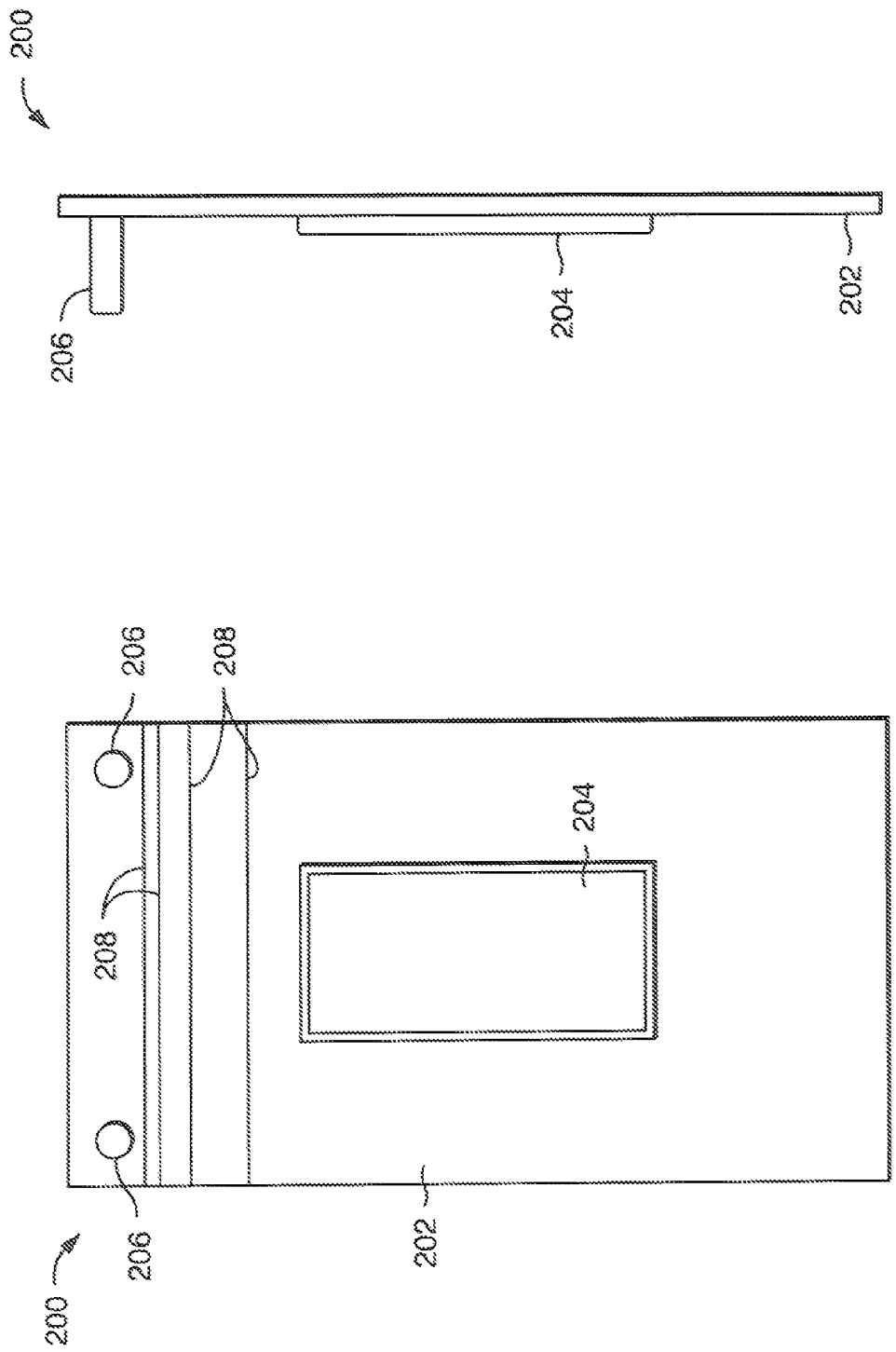

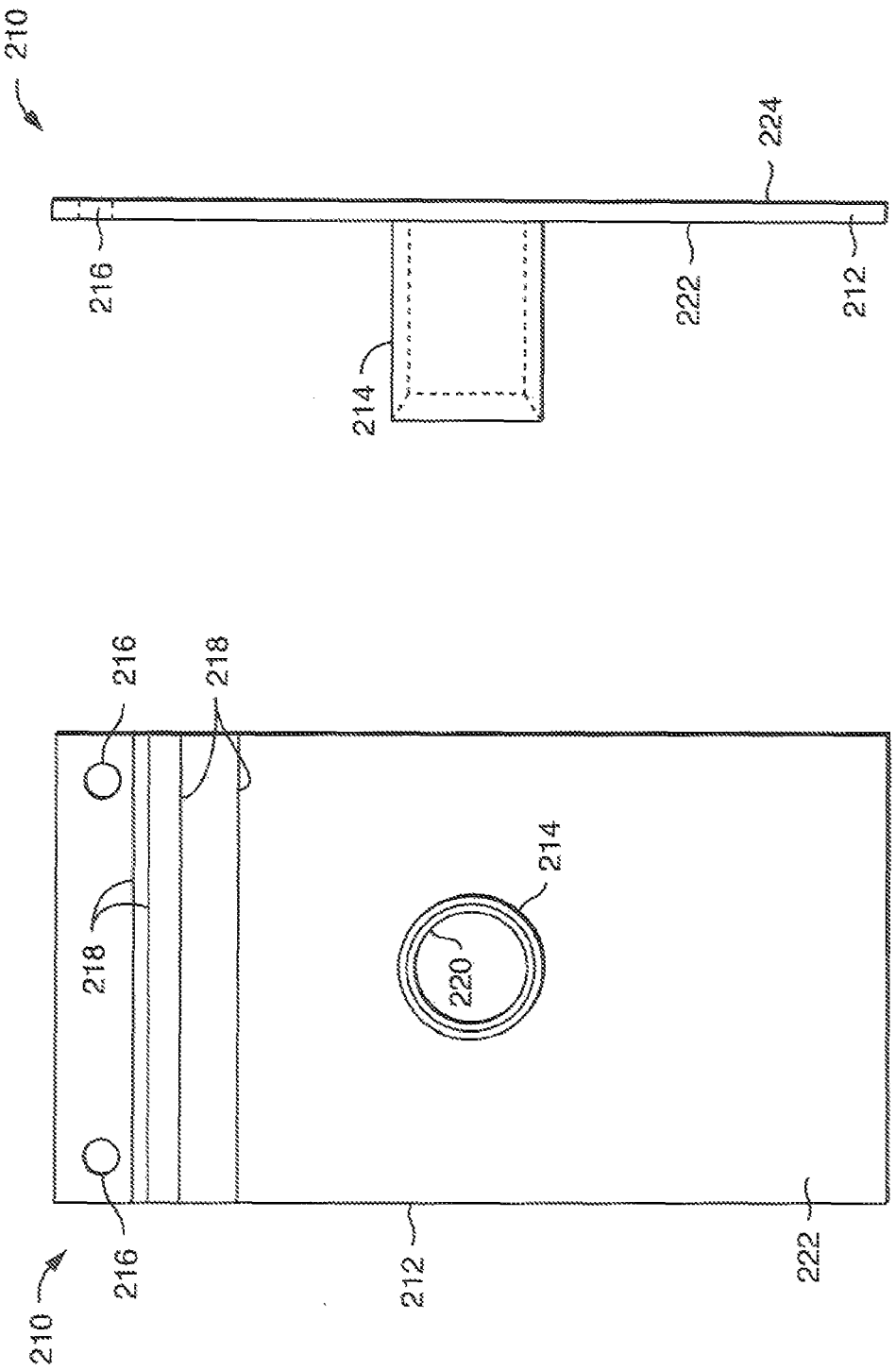

ABSORBENT ARTICLE WITH POINT FUSION BONDING

BACKGROUND

It is desired that the attributes of personal care absorbent articles include low leakage of liquid waste from the absorbent article and a dry feel to the wearer. In addition to the desired attributes of low leakage and dry feel, it is desired that absorbent articles possess a feeling of softness on the bodyside surface. Absorbent articles, however, traditionally fail to possess the combination of the desired attributes. Absorbent articles commonly fail before the total absorbent capacity of the absorbent article is utilized. Problems which can typically exist can be with regards to the ability of the bodyside liner to allow quick intake in one direction towards an absorbent body while preventing return of fluid in the opposite direction. The rate at which intake occurs generally determines whether leakage is reduced or whether body fluids are appropriately contained. An insufficient rate of fluid intake by the absorbent body, especially on the second, third or fourth micturition, insufficient containment of fluids, and/or saturation of the absorbent body in the target area can each result in leakage of fluids from the absorbent article and a persistent wetness in the area of the absorbent article on the skin of the wearer. Additionally, fibers that have typically been utilized to impart softness to the bodyside surface have trapped moisture at the bodyside surface and, therefore, have persisted the feeling of wetness on the skin of the wearer.

It has been found that urination can occur at rates as high as 15 to 20 milliliters per second and at velocities as high as 280 centimeters per second. Conventional absorbent structures, such as those comprising admixtures of absorbent gelling particles and cellulosic fluffed pulp, may initially intake fluid at rates of only about 8 milliliters per second or less, depending on the web density and concentration of gelling particles. The initial intake rates, however, for conventional absorbent articles can deteriorate once they have already received liquid surges into their absorbent body. The disparity between liquid delivery and intake rates can result in excessive pooling on the surface of the absorbent article before it is taken up by the absorbent body. Such pooled fluid can wet the wearer's skin, leak from the leg and waist openings of the absorbent article, and soil the outer clothing or bedding of the wearer. Attempts to alleviate leaking and to provide dryness to the wearer of the absorbent article have included changing the amount or configuration of the absorbent material of the absorbent body. For example, thick, lofty fabric structures have been utilized in an effort to absorb the fluid and to keep the body skin separated from the wet absorbent body. However, many of these structures can lose resiliency and collapse when wetted. The collapse of these structures can lower liquid intake and storage capacity resulting in wet skin of the wearer.

There remains a need for an absorbent structure that can adequately reduce the incidence of leakage from absorbent articles, such as diapers. There remains a need for an absorbent structure which can provide improved handling of liquid and more effectively intake and retain loadings of liquid during use. There remains a need for an absorbent structure that can minimize the amount of moisture in contact with the wearer's skin and provide a feeling of softness on the skin of the wearer.

SUMMARY

In an embodiment, an absorbent article can have a backsheet layer; an absorbent body which can be superposed on the backsheet layer, the absorbent body can have a wearer facing surface and a garment facing surface; a fluid transfer layer bonded to the absorbent body, the fluid transfer layer can have at least one material which can be hydraulically entangled into a nonwoven substrate; an acquisition layer bonded to the fluid transfer layer; and a bodyside liner point fusion bonded with the acquisition layer, the bodyside liner can have a wearer facing layer and a garment facing layer. In an embodiment, the absorbent body can have greater than about 50% of a superabsorbent material. In an embodiment, the fluid transfer layer can have at least two materials which are hydraulically entangled into a nonwoven substrate. In an embodiment, the fluid transfer layer can be bonded with the acquisition layer via adhesive. In an embodiment, at least one of pressure bonding, thermal bonding, and ultrasonic bonding can be utilized to point fusion bond the bodyside liner to the acquisition layer. In an embodiment, the point fusion bonding can be ultrasonic bonding with a bond pattern providing from about 20 to about 100 bond points per square inch. In an embodiment, the absorbent article can have a surface moisture of less than 0.6 g.

In an embodiment, an absorbent article can have a backsheet layer; an absorbent body which can be superposed on the backsheet layer, the absorbent body can have greater than about 50% superabsorbent material; a fluid transfer layer bonded to the absorbent body, the fluid transfer layer can have at least one material which can be hydraulically entangled into a nonwoven substrate; an acquisition layer bonded to the fluid transfer layer; and a bodyside liner point fusion bonded with the acquisition layer, the bodyside liner can have a bonded carded web which can have a first layer and a second layer. In an embodiment, the fluid transfer layer can have at least two materials which are hydraulically entangled into a nonwoven substrate. In an embodiment, one of the first and second layers of the bodyside liner can have fibers which can have a denier of about 1.5 and the other of the first and second layers of the bodyside liner can have fibers which can have a denier of about 2. In an embodiment, the fluid transfer layer can be bonded with the acquisition layer via adhesive. In an embodiment, at least one of pressure bonding, thermal bonding, and ultrasonic bonding can be utilized to point fusion bond the bodyside liner to the acquisition layer. In an embodiment, the point fusion bonding can be ultrasonic bonding with a bond pattern providing from about 20 to about 100 bond points per square inch. In an embodiment, the absorbent article can have a surface moisture of less than 0.6 g.

In an embodiment, an absorbent article can have a backsheet layer; an absorbent body which can be superposed on the backsheet layer, the absorbent body can have a wearer facing surface and a garment facing surface and can have greater than about 50% superabsorbent material; a fluid transfer layer bonded to the wearer facing surface of the absorbent body via adhesive bonding, the fluid transfer layer can have at least one material which can be hydraulically entangled into a nonwoven substrate; an acquisition layer bonded to the fluid transfer layer via adhesive bonding; and a bodyside liner bonded with the acquisition layer via ultrasonic bonding, the bodyside liner can have a wearer facing layer and a garment facing layer wherein at least one of the wearer facing and garment facing layers can have fibers which can have a denier of about 1.5 and the other of the wearer facing and garment facing layers can have fibers which can have a denier of about 2. In an embodiment, the fluid transfer layer can have at least two materials which are hydraulically entangled into a nonwoven substrate. In an embodiment, the fluid transfer layer can be further bonded with the garment facing surface of the absorbent body. In an embodiment, the ultrasonic bonding can have a bond pattern providing from about 20 to about 100 bond points per square inch. In an embodiment, the ultrasonic bonding can have a bond pattern providing from about 5% to about 30% bonded area. In an embodiment, the absorbent article can have a surface moisture of less than 0.6 g.

BRIEF DESCRIPTION OF THE DRAWINGS

FIG. 11A and FIG. 11B are a top view and side view, respectively, of a bottom base board employed in surface moisture testing.

FIG. 12A and FIG. 12B are a top view and a side view, respectively, of a top board employed in surface moisture testing.

DETAILED DESCRIPTION

Figure 1:
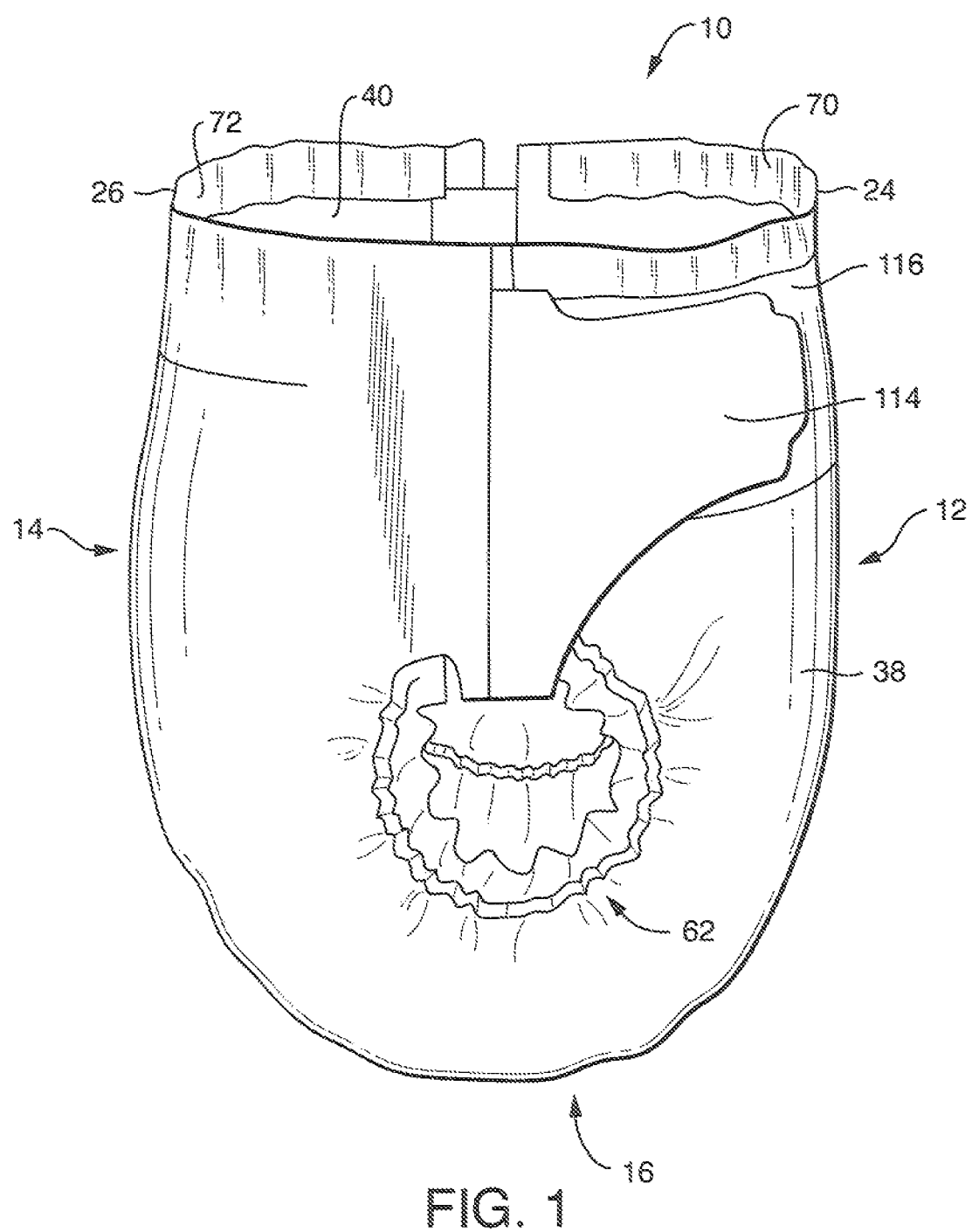
FIG. 1 is a side view illustration of an embodiment of an absorbent article.

In an embodiment, the present disclosure is generally directed towards an absorbent article which can have improved intake and retention of liquid waste. In an embodiment, the present disclosure is generally directed towards an absorbent article which can reduce the amount of moisture in contact with the skin of the wearer.

Definitions

The term "absorbent article' refers herein to an article which may be placed against or in proximity to the body (i.e., contiguous with the body) of the wearer to absorb and contain various liquid and solid wastes discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, incontinence products, medical garments, surgical pads and bandages, other personal care or health care garments, and the like without departing from the scope of the present disclosure.

The term "acquisition layer" refers herein to a layer capable of accepting and temporarily holding liquid body waste to decelerate and diffuse a surge or gush of liquid body waste and to subsequently release the liquid body waste therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which the liquid body waste, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. which is incorporated herein by reference. Meltblown fibers are microfibers which may be continuous or discontinuous, are generally smaller than about 0.6 denier, and may be self-bonding when deposited onto a collecting surface.

The term "non-woven" refers herein to materials and webs of material which are formed without the aid of a textile weaving or knitting process.

The term "pliable' refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6 and about 10.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

Absorbent Article:

Referring to FIG. 1, a disposable absorbent article 10 of the present disclosure is exemplified in the form of a wearer's diaper. While the embodiments and illustrations described herein may generally apply to absorbent articles manufactured in the product longitudinal direction, which is hereinafter called the machine direction manufacturing of a product, it should be noted that one of ordinary skill could apply the information herein to absorbent articles manufactured in the latitudinal direction of the product which hereinafter is called the cross direction manufacturing of a product without departing from the spirit and scope of the disclosure. The absorbent article 10 includes a front waist region 12, a back waist region 14, and a crotch region 16 interconnecting the front and back waist regions, 12 and 14, respectively. The absorbent article 10 has a pair of longitudinal side edges, 20 and 22 (shown in FIG. 2), and a pair of opposite waist edges, respectively designated front waist edge 24 and back waist edge 26. The front waist region 12 can be contiguous with the front waist edge 24 and the back waist region 14 can be contiguous with the back waist edge 26.

Figure 2:
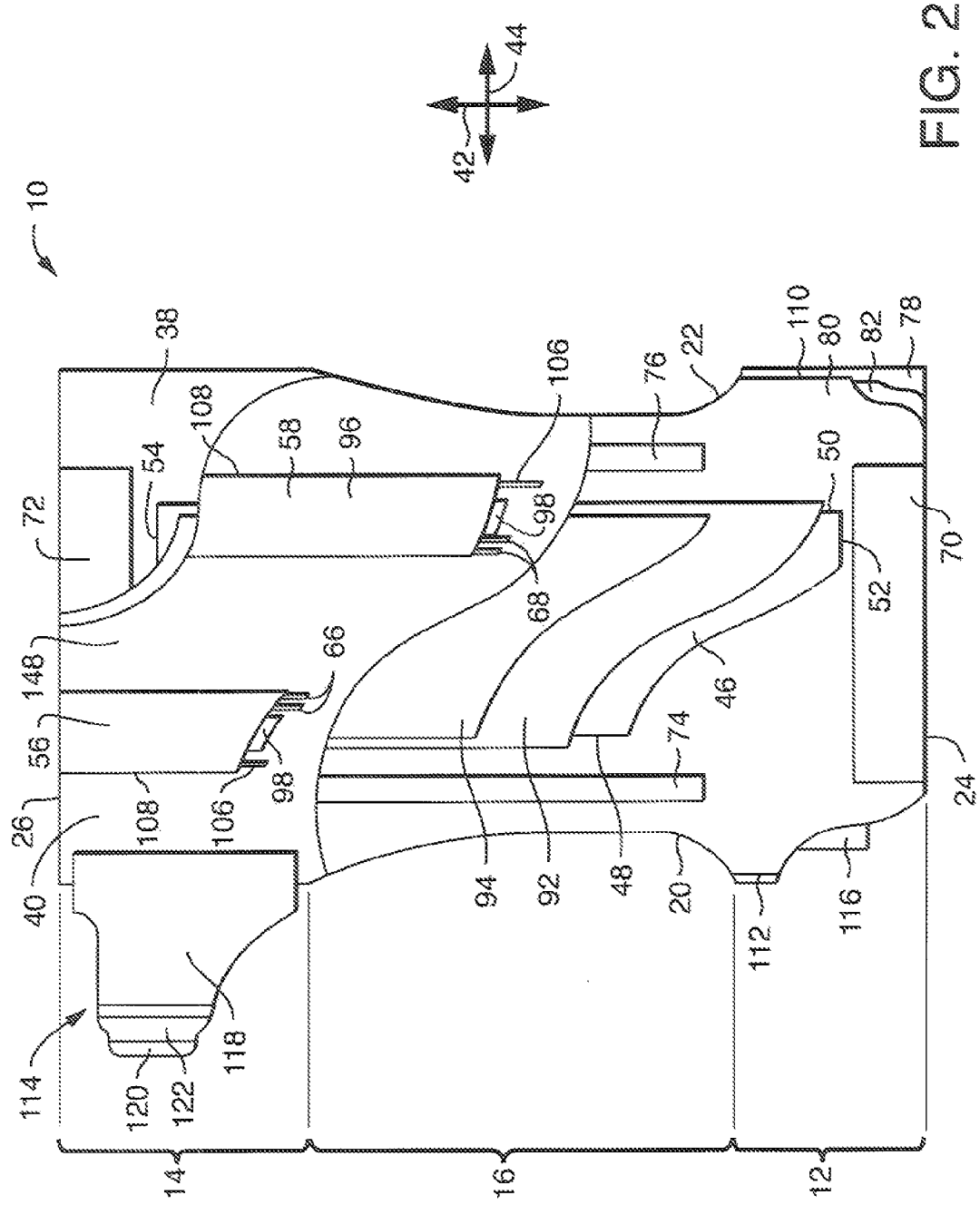
FIG. 2 is a top view illustration of an embodiment of the absorbent article of FIG. 1 in an unfolded, flat-out, uncontracted state (i.e., with all elastic induced gathering and contractions removed), with the bodyside liner facing the viewer and portions partially cut away to illustrate underlying features.

Referring to FIG. 2, the absorbent article 10 is illustrated in a stretched and laid flat configuration. The absorbent article 10 can include an outer cover 38 and a bodyside liner 40 which can be bonded to the outer cover 38 in a superposed relation by any suitable means such as, but not limited to, adhesives, ultrasonic bonds, thermal bonds, pressure bonds, or other conventional techniques. The outer cover 38 can define a length, or longitudinal direction 42, and a width, or lateral direction 44, which, in the illustrated embodiment, can coincide with the length and width of the absorbent article 10. An absorbent body 46 can be disposed between the outer cover 38 and the bodyside liner 40. The absorbent body 46 can have longitudinal edges, 48 and 50, which, in an embodiment, can form portions of the longitudinal side edges, 20 and 22, respectively, of the absorbent article 10 and can have opposite end edges, 52 and 54, which, in an embodiment, can form portions of the waist edges, 24 and 26, respectively, of the absorbent article 10. In an embodiment, the absorbent body 46 can have a length and width that are the same as or less than the length and width of the absorbent article 10. A pair of containment flaps, 56 and 58, can be secured to the bodyside liner 40 for inhibiting the lateral flow of body wastes.

The front waist region 12 can include the portion of the absorbent article 10 that, when worn, is positioned at least in part on the front of the wearer while the back waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 24 and 26, of the absorbent article 10 are configured to encircle the waist of the wearer and together define the central waist opening 60. Portions of the longitudinal side edges, 20 and 22, in the crotch region 16 can generally define leg openings, 62 (shown in FIG. 1) and 64 (shown in FIG. 10), when the absorbent article 10 is worn.

The absorbent article 10 can be configured to contain and/or absorb liquid and solid wastes discharged from the wearer. For example, the containment flaps, 56 and 58, can be configured to provide a barrier to the lateral flow of body exudates. A flap elastic member, 66 and 68, can be operatively joined to each containment flap, 56 and 58, in any suitable manner known in the art. The elasticized containment flaps, 56 and 58, can define a partially unattached edge that can assume an upright configuration in at least the crotch region 16 of the absorbent article 10 to form a seal against the wearer's body. The containment flaps, 56 and 58, can be located along the absorbent article 10 longitudinal side edges, 20 and 22, and can extend longitudinally along the entire length of absorbent article 10 or can extend partially along the length of the absorbent article 10. Suitable construction and arrangements for containment flaps, 56 and 58, are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 10 can suitably include a front waist elastic member 70, a rear waist elastic member 72, and leg elastic members, 74 and 76, as are known to those skilled in the art. The waist elastic members, 70 and 72, can be attached to the outer cover 38 and/or the bodyside liner 40 along the opposite waist edges, 24 and 26, and can extend over part or all of the waist edges, 24 and 26. The leg elastic members, 74 and 76, can be attached to the outer cover 38 and/or the bodyside liner 40 along the opposite longitudinal side edges, 20 and 22, and positioned in the crotch region 16 of the absorbent article 10.

In an embodiment, the absorbent article 10 can have a surface moisture of less than about 0.6 grams. In an embodiment, the absorbent article 10 can have a surface moisture of less than about 0.6, 0.55, 0.5, 0.45, 0.4, 0.35, 0.3, 0.25, 0.2, 0.15, 0.1, 0.09, 0.08, 0.07, 0.06, or 0.05 grams.

Figure 3:
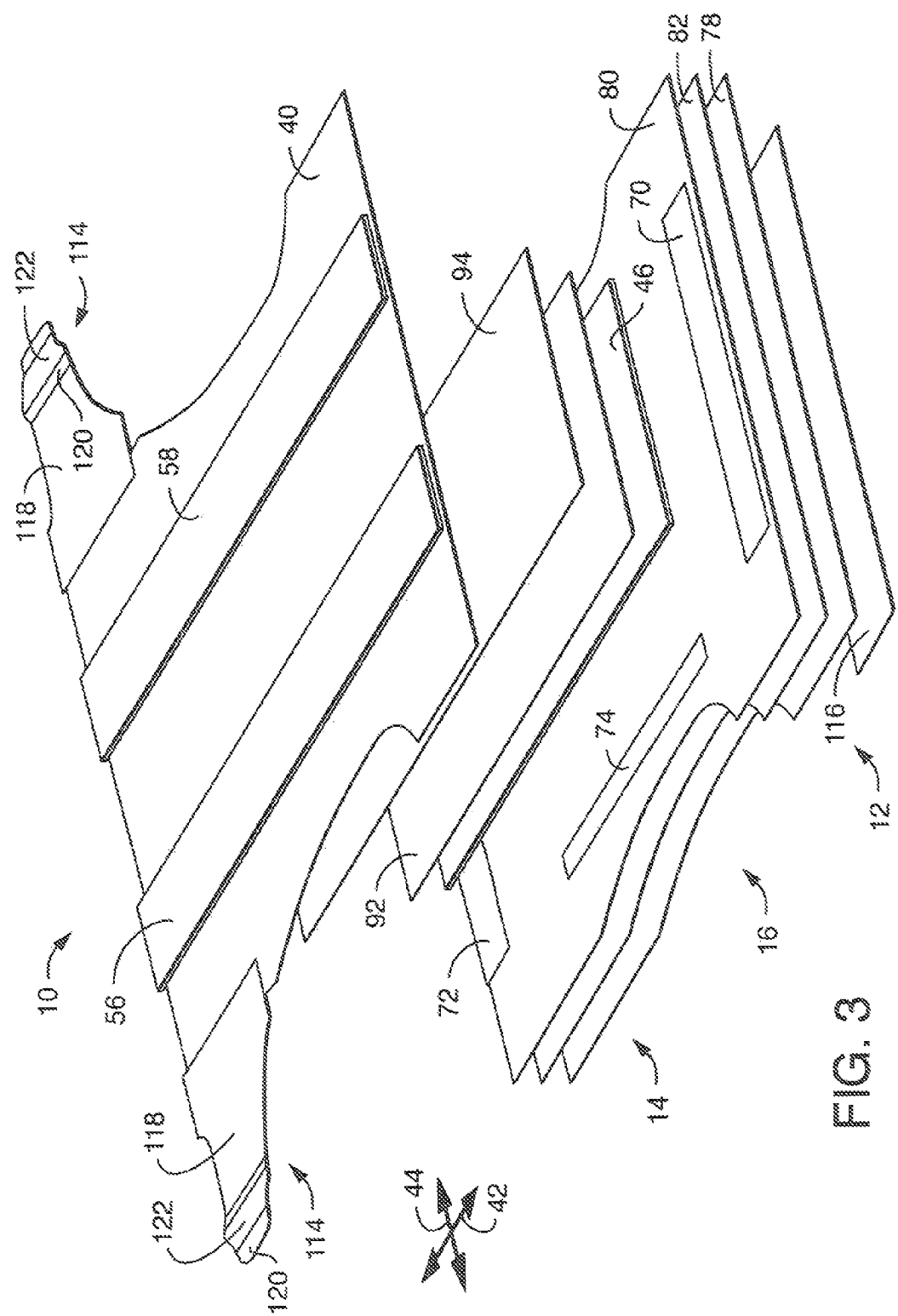
FIG. 3 is an exploded view of the absorbent article of FIG. 2.
Figure 4:
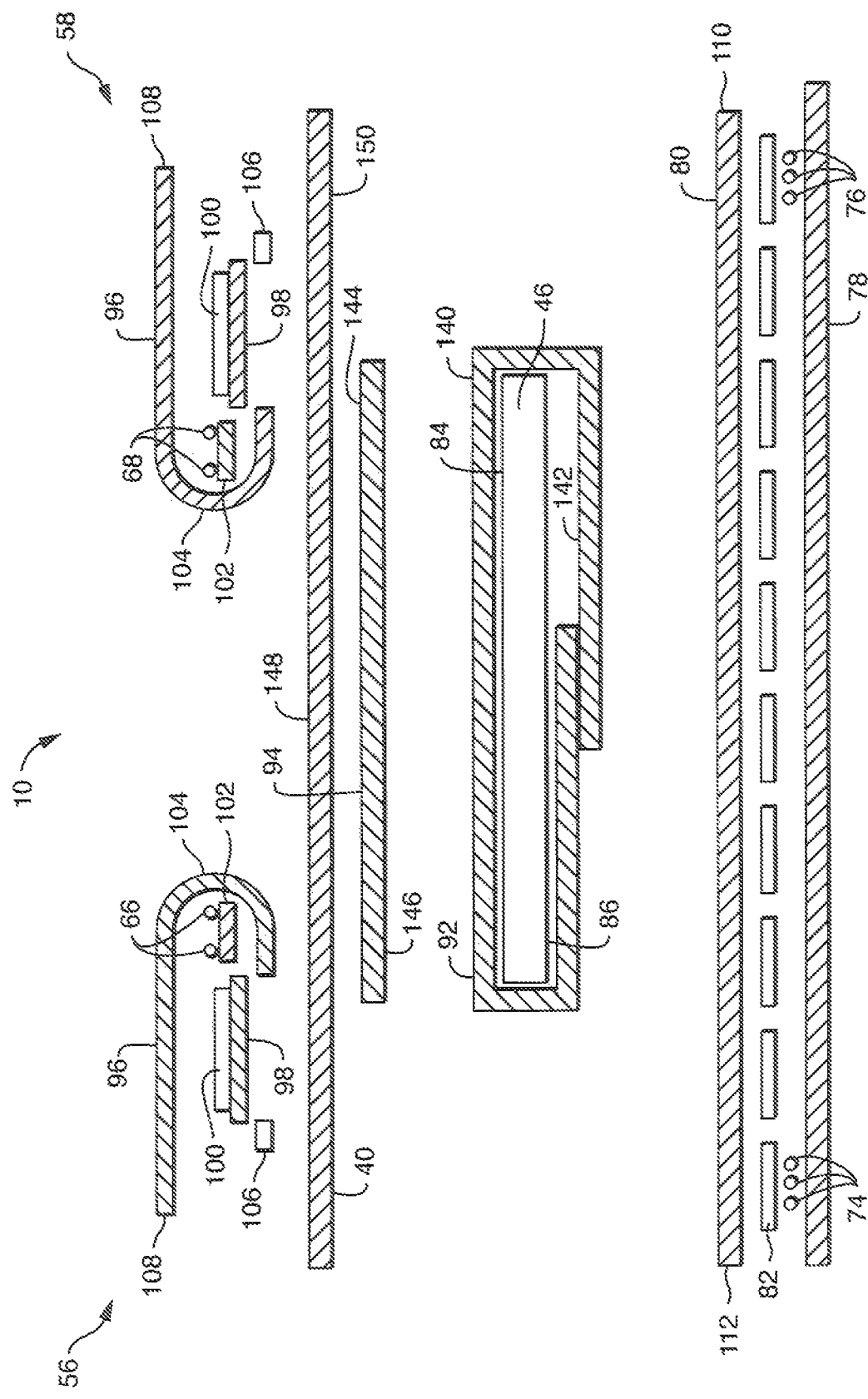
FIG. 4 is a cross-section view of another embodiment of the absorbent article of FIG. 1.
Figure 5:
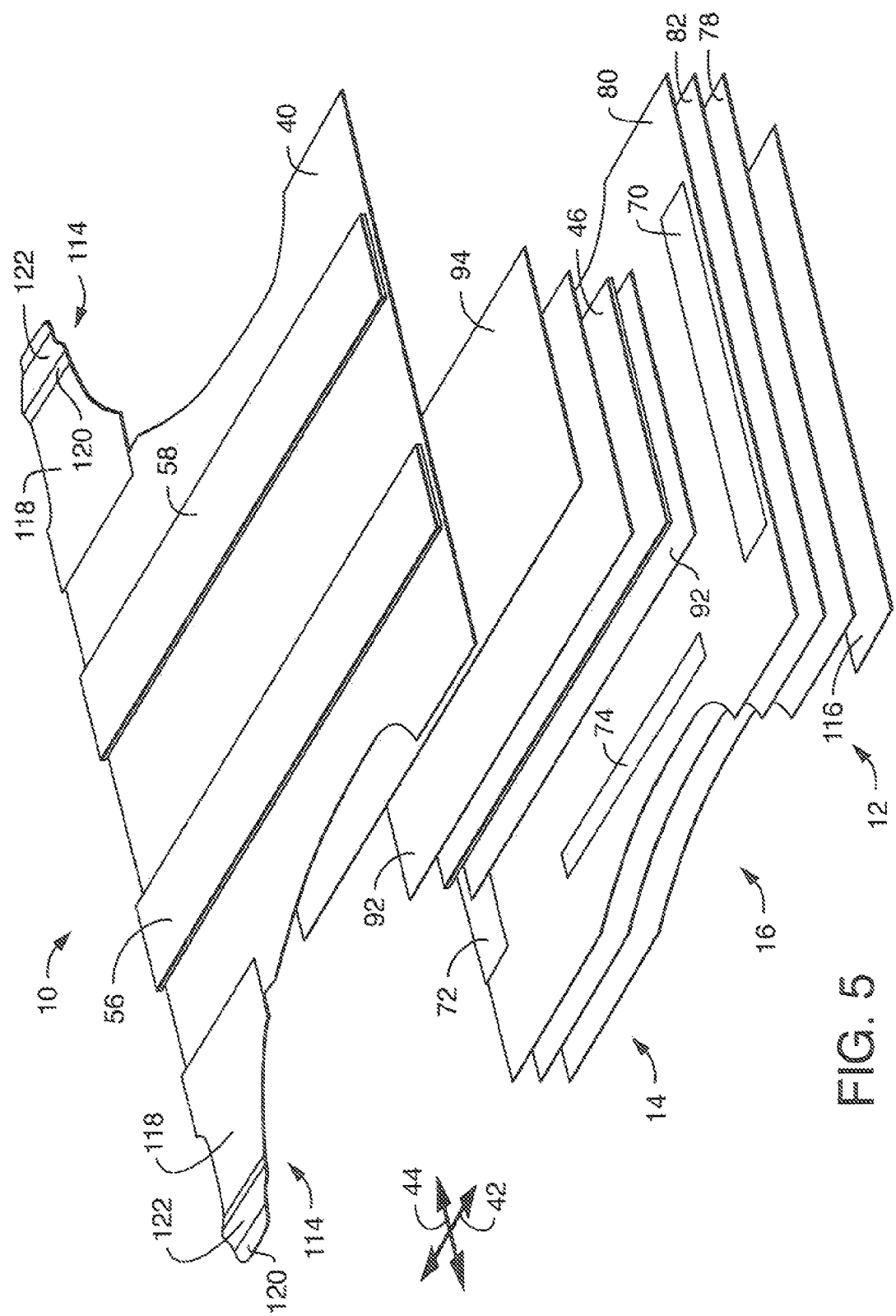
FIG. 5 is an exploded view of another embodiment of the absorbent article of FIG. 1.
Figure 6:
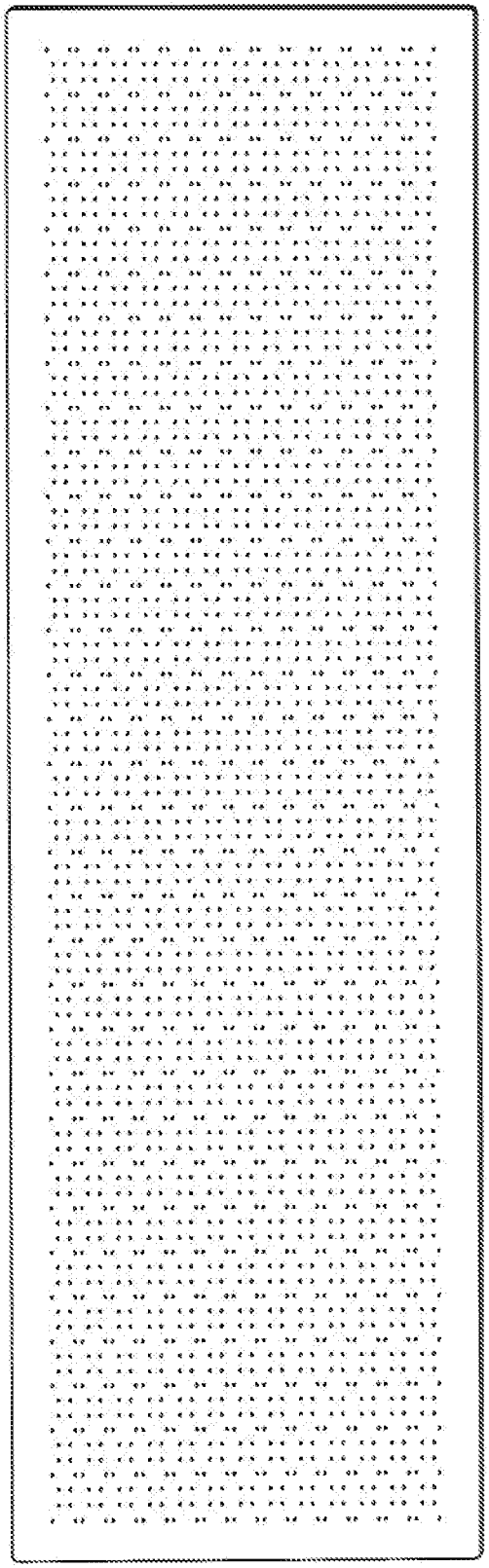
FIG. 6 is a top view illustration of an embodiment of a bonding pattern.
Figure 7:
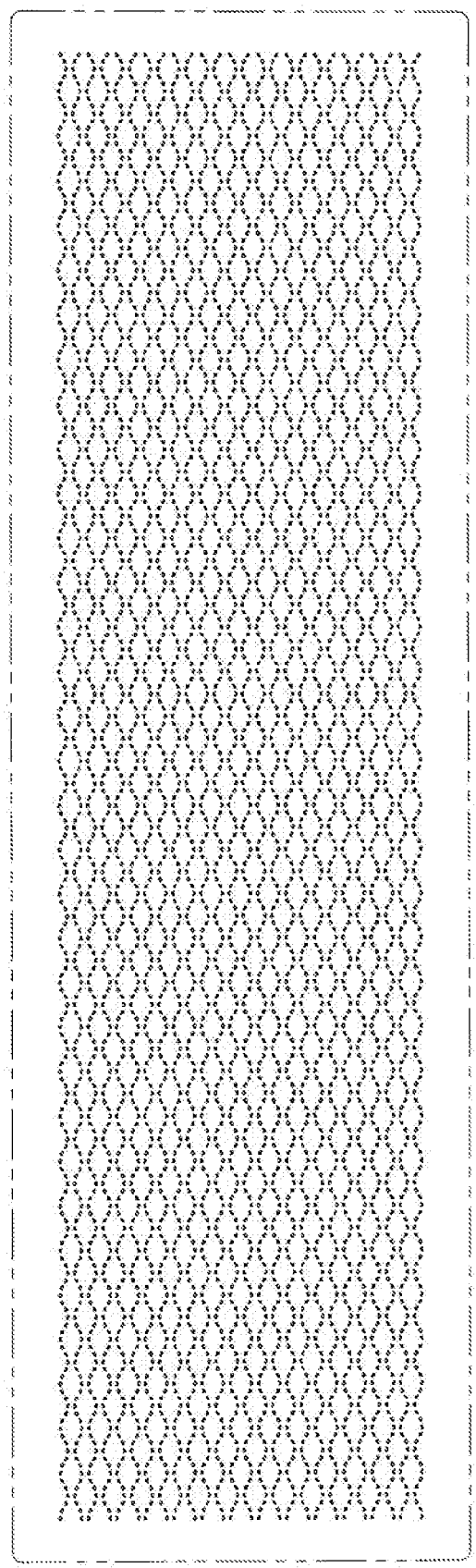
FIG. 7 is a top view illustration of an embodiment of a bonding pattern.
Figure 8:
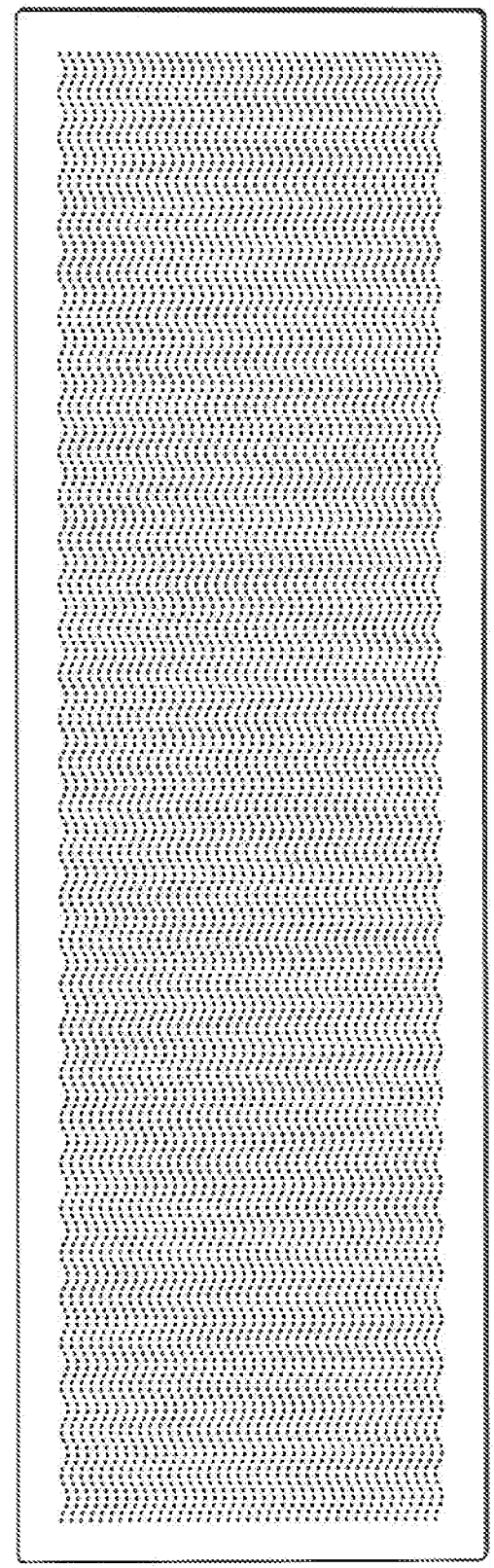
FIG. 8 is a top view illustration of an embodiment of a bonding pattern.
Figure 9:
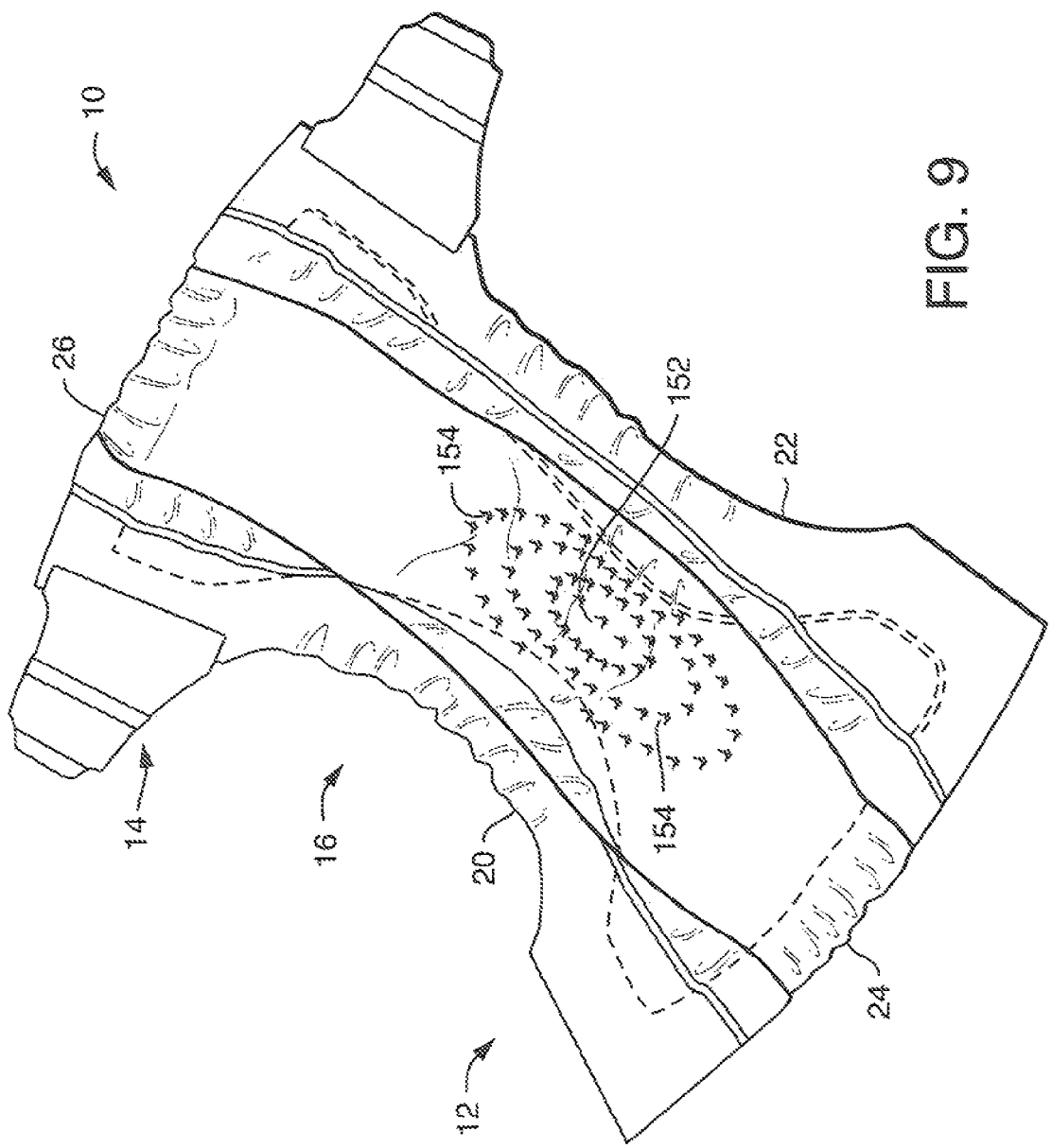
FIG. 9 is a top view of an embodiment of point fusion bonding in a target area of an absorbent article.
Figure 10:
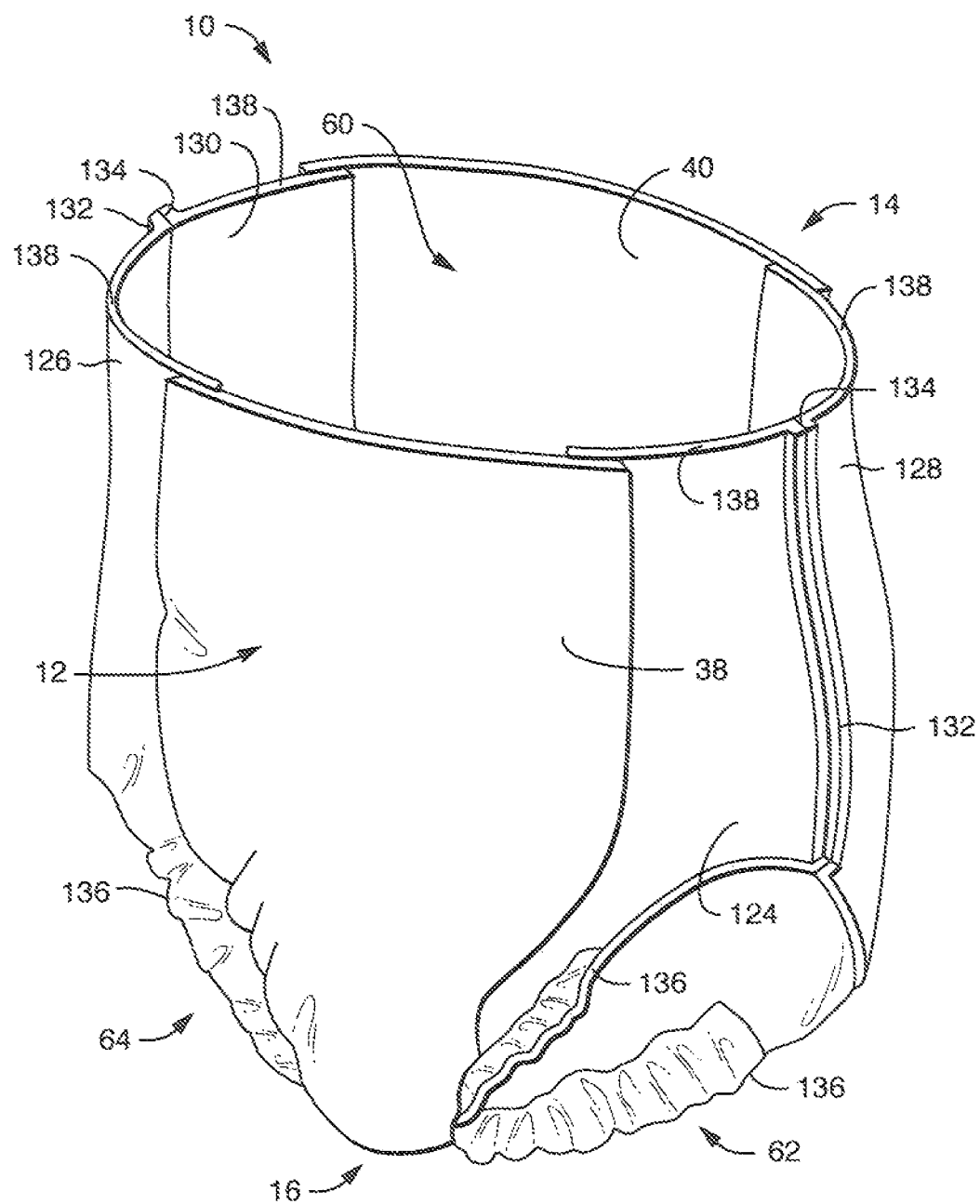
FIG. 10 is a perspective view of an embodiment of an absorbent article.

Additional details regarding each of these elements of the absorbent article 10 described herein can be found below and with reference to FIG. 1-10. FIG. 3 is an exploded view of the absorbent article of FIG. 2. FIG. 4 is a cross-sectional view of another embodiment of the absorbent article of FIG. 1. FIG. 5 is an exploded view of another embodiment of the absorbent article of FIG. 1. FIGS. 6-8 are top view illustrations of non-limiting embodiments of point fusion bonding patterns. FIG. 9 is a top view of an embodiment of point fusion bonding in a target area of an absorbent article. FIG. 10 is a perspective view of an embodiment of an absorbent article.

Outer Cover:

The outer cover 38 can be breathable and/or liquid impermeable. The outer cover 38 can be elastic, stretchable or non-stretchable. The outer cover 38 may be constructed of a single layer, multiple layers, laminates, spunbond fabrics, films, meltblown fabrics, elastic netting, microporous webs, bonded-carded webs or foams provided by elastomeric or polymeric materials. In an embodiment, the outer cover 38 can be a single layer of a liquid impermeable material. In an embodiment, the outer cover 38 can be suitably stretchable, and more suitably elastic, in at least the lateral or circumferential direction 44 of the absorbent article 10. In an embodiment, the outer cover 38 can be stretchable, and more suitably elastic, in both the lateral 44 and the longitudinal 42 directions. In an embodiment, the outer cover 38 can be a multi-layered laminate in which at least one of the layers is liquid impermeable. In an embodiment, the outer cover 38 may be a two layer construction, including an outer layer 78 constructed of a liquid permeable material and an inner layer 80 constructed of liquid impermeable material bonded together by a laminate adhesive 82. Suitable laminate adhesives can be applied continuously or intermittently as beads, a spray, parallel swirls, or the like. Suitable adhesives can be obtained from Bostik Findlay Adhesives, Inc. of Wauwatosa, Wis., U.S.A. It is to be understood that the inner layer 80 can be bonded to the outer layer 78 utilizing ultrasonic bonds, thermal bonds, pressure bonds, or the like.

The liquid permeable outer layer 78 of the outer cover 38 can be any suitable material and may be one that provides a generally cloth-like texture to the wearer. An example of such material can be a 100% polypropylene bonded-carded web with a diamond bond pattern available from Sandler A. G., Germany such as 30 gsm Sawabond 4185® or equivalent. Another example of material suitable for use as an outer layer 78 of an outer cover 38 can be a 20 gsm spunbond polypropylene non-woven web. The outer layer 78 may also be constructed of the same materials from which the bodyside liner 40 is constructed as described herein. It is to be understood that it is not necessary for the outer layer 78 of the outer cover 38 to be liquid permeable.

The liquid impermeable inner layer 80 of the outer cover 38 can be either vapor permeable (i.e., "breathable") or vapor impermeable. The inner layer 80 may be manufactured from a thin plastic film, although other liquid impermeable materials may also be used. The liquid impermeable inner layer 80 (or the liquid impermeable outer cover 38 where the outer cover 38 is of a single-layer construction) can inhibit liquid body waste from leaking out of the absorbent article 10 and wetting articles, such as bed sheets and clothing, as well as the wearer and caregiver. An example of a material for an inner layer 80 can be a printed 19 gsm Pliant XP-8695H film or equivalent commercially available from Pliant Corporation, Schaumburg, Ill., U.S.A.

Where the outer cover 38 is of a single layer construction, it can be embossed and/or matte finished to provide a more cloth-like appearance. The outer cover 38 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 46 can be suitably constructed to be generally compressible, conformable, pliable, non-irritating to the wearer's skin and capable of absorbing and retaining liquid body waste, such as urine. The absorbent body 46 can be manufactured in a wide variety of sizes and shapes (for example, rectangular, trapezoidal, T-shape, I-shape, hourglass shape, etc.) and from a wide variety of materials. The size and the absorbent capacity of the absorbent body 46 should be compatible with the size of the intended wearer and the liquid loading imparted by the intended use of the absorbent article 10. Additionally, the size and the absorbent capacity of the absorbent body 46 can be varied to accommodate wearers ranging from infants to adults.

The absorbent body 46 may have a length ranging from about 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm. The absorbent body 46 may have a crotch width ranging from about 50, 55, 60, 65, or 70 mm to about 75, 80, 85, 90, 95, 100, 105, 110, 115, 120, 125, 130, 140, 150, 160, 170 or 180 mm. The width of the absorbent body 46 located within the front waist region 12 and/or the back waist region 14 of the absorbent article 10 may range from about 80, 85, 90, or 95 mm to about 100, 105, 110, 115, 120, 125 or 130 mm. As noted herein, the absorbent body 46 can have a length and width that can be less than the length and width of the absorbent article 10.

In an embodiment, the absorbent article 10 can be a diaper having the following ranges of lengths and widths of an absorbent body 46 having an hourglass shape: the length of the absorbent body 46 may range from about 200, 210, 220, 225, 240 or 250 mm to about 260, 280, 300, 310, 320, 330, 340, 350, 355, 360, 380, 385, or 390 mm; the width of the absorbent body 46 in the crotch region 16 may range from about 50, 55, or 60 mm to about 65, 70, 75, or 80 mm; the width of the absorbent body 46 in the front waist region 12 and/or the back waist region 14 may range from about 80, 85, 90, or 95 mm to about 100, 105, or 110 mm.

In an embodiment, the absorbent article 10 may be a training pant or youth pant having the following ranges of lengths and widths of an absorbent body 46 having an hourglass shape: the length of the absorbent body 46 may range from about 400, 410, 420, 440 or 450 mm to about 460, 480, 500, 510 or 520 mm; the width of the absorbent body 46 in the crotch region 16 may range from about 50, 55, or 60 mm to about 65, 70, 75, or 80 mm; the width of the absorbent body 46 in the front waist region 12 and/or the back waist region 14 may range from about 80, 85, 90, or 95 mm to about 100, 105, 110, 115, 120, 125, or 130 mm.

In an embodiment, the absorbent article 10 can be an adult incontinence garment having the following ranges of lengths and widths of an absorbent body 46 having a rectangular shape: the length of the absorbent body 46 may range from about 400, 410 or 415 to about 425 or 450 mm; the width of the absorbent body 46 in the crotch region 16 may range from about 90, or 95 mm to about 100, 105, or 110 mm. It should be noted that the absorbent body 46 of an adult incontinence garment may or may not extend into either or both the front waist region 12 or the back waist region 14 of the absorbent article 10.

The absorbent body 46 can have two surfaces, 84 and 86, such as a wearer facing surface 84 and a garment facing surface 86. Side edges, such as longitudinal side edges, 48 and 50, and such as front and back end edges, 52 and 54, can connect the two surfaces, 84 and 86.

In an embodiment, the absorbent body 46 can be composed of a web material of hydrophilic fibers, cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In an embodiment, the absorbent body 46 can be a matrix of cellulosic fluff and superabsorbent hydrogel-forming particles. The absorbent body 46 may be constructed of a single layer of materials, or in the alternative, may be constructed of two layers of materials or more.

In an embodiment in which the absorbent body 46 has two layers, the absorbent body 46 can have a wearer facing layer suitably composed of hydrophilic fibers and a garment facing layer suitably composed of at least in part of a high absorbency material commonly known as superabsorbent material. In an embodiment, the wearer facing layer of the absorbent body 46 can be suitably composed of cellulosic fluff, such as wood pulp fluff, and the garment facing layer of the absorbent body 46 can be suitably composed of superabsorbent hydrogel-forming particles, or a mixture of cellulosic fluff and superabsorbent hydrogel-forming particles. As a result, the wearer facing layer can have a lower absorbent capacity per unit weight than the garment facing layer. The wearer facing layer may alternatively be composed of a mixture of hydrophilic fibers and superabsorbent material, as long as the concentration of superabsorbent material present in the wearer facing layer is lower than the concentration of superabsorbent material present in the garment facing layer so that the wearer facing layer can have a lower absorbent capacity per unit weight than the garment facing layer. It is also contemplated that the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent body 46 with a lower absorbent capacity in the wearer facing layer than in the garment facing layer.

Various types of wettable, hydrophilic fibers can be used in the absorbent body 46. Examples of suitable fibers include cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other hydrophilic fiber materials, such as synthetic, polymeric, or meltblown fibers or with a combination of meltblown and natural fibers.

In an embodiment, the cellulosic fluff can include a blend of wood pulp fluff. An example of wood pulp fluff can be "Bowater CoosAbsorb S Fluff Pulp" or equivalent available from Bowater, Greenville, S.C., U.S.A. which is a bleached, highly absorbent sulfate wood pulp containing primarily southern soft wood fibers. The absorbent web can be formed with a dry-forming technique, an air forming technique, a wet-forming technique, a foam-forming technique, or the like, as well as combinations thereof. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. In an embodiment, the superabsorbent material can absorb more than 24 times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent body 46. In an embodiment, the absorbent body 46 can have at least about 50% by weight of a superabsorbent material. In an embodiment, the absorbent body 46 can have at least about 50, 55, 60, 65, 70, 75, 80, 85, 90, 95, 99 or 100% by weight of a superabsorbent material. Examples of superabsorbent material include, but are not limited to, FAVOR SXM-9300 or equivalent available from Evonik Industries, Greensboro, N.C., U.S.A. and HYSORB 8760 or equivalent available from BASF Corporation, Charlotte, N.C., U.S.A.

The absorbent body 46 can be superposed over the inner layer 80 of the outer cover 38, extending laterally between the leg elastic members, 74 and 76, and can be bonded to the inner layer 80 of the outer cover 38, such as by being bonded thereto with adhesive. However, it is to be understood that the absorbent body 46 may be in contact with, and unbounded with, the outer cover 38 and remain within the scope of this disclosure.

Fluid Transfer Layer:

In an embodiment, the absorbent article 10 can have a fluid transfer layer 92. The fluid transfer layer 92 can have a wearer facing surface 140 and a garment facing surface 142. In an embodiment, the garment facing surface 142 of the fluid transfer layer 92 can be bonded to the wearer facing surface 84 of the absorbent body 46. Bonding of the garment facing surface 142 of the fluid transfer layer 92 to the wearer facing surface 84 of the absorbent body 46 can occur through the use of adhesive. In an embodiment, such as, for example, in the non-limiting illustration of FIG. 4, the fluid transfer layer 92 can completely encompass the absorbent body 46 and can be sealed to itself. In an embodiment, the fluid transfer layer 92 may be folded over on itself and then sealed using, for example, heat and/or pressure. In an embodiment, such as, for example, in the non-limiting illustration of FIG. 5, the fluid transfer layer 92 may be composed of separate sheets of material which can be utilized to partially or fully encompass the absorbent body 46 and which can be sealed together using a sealing means such as an ultrasonic bonder or other thermochemical bonding means or the use of an adhesive.

In an embodiment, the fluid transfer layer 92 can be bonded with only the wearer facing surface 84 of the absorbent body 46. In an embodiment, the fluid transfer layer 92 can be bonded with the wearer facing surface 84 and at least one of the edges, 48, 50, 52 and/or 54, of the absorbent body 46. In an embodiment, the fluid transfer layer 92 can be bonded with the wearer facing surface 84, at least one of the edges, 48, 50, 52 and/or 54, and the garment facing surface 86 of the absorbent body 46. In an embodiment, the absorbent body 46 may be partially or completely encompassed by the fluid transfer layer 92.

The fluid transfer layer 92 can be pliable, less hydrophilic than the absorbent body 46, and sufficiently porous to be liquid permeable to thereby permit liquid to penetrate through its thickness to reach the absorbent body 46. In an embodiment, the fluid transfer layer 92 can have sufficient structural integrity to withstand wetting thereof and of the absorbent body 46. In an embodiment, the fluid transfer layer 92 can be constructed from a single layer of material or it may be a laminate constructed from two or more layers of material.

A common fluid transfer layer is an absorbent cellulosic material such as creped wadding or a high-strength tissue. A disadvantage of this common type of fluid transfer layer is a deficiency of wet strength to maintain structural integrity of the absorbent body 46. In an embodiment, the fluid transfer layer 92 can be a laminate of a meltblown nonwoven material having fine fibers, laminated to at least one, spunbond nonwoven material layer having coarse fibers. In such an embodiment, the fluid transfer layer 92 can be a spunbond-meltblown ("SM") material. In an embodiment, the fluid transfer layer 92 can be a spunbond-meltblown-spunbond ("SMS") material. A non-limiting example of such a fluid transfer layer 92 can be a 10 gsm spunbond-meltblown-spunbond material. In an embodiment, the fluid transfer layer 92 can be composed of at least one material which has been hydraulically entangled into a nonwoven substrate. In an embodiment, the fluid transfer layer 92 can be composed of at least two materials which have been hydraulically entangled into a nonwoven substrate. In an embodiment, the fluid transfer layer 92 can have at least three materials which have been hydraulically entangled into a nonwoven substrate. A non-limiting example of a fluid transfer layer 92 can be a 33 gsm hydraulically entangled substrate. In such an example, the fluid transfer layer 92 can be a 33 gsm hydraulically entangled substrate composed of a 12 gsm spunbond material, a 10 gsm wood pulp material having a length from about 0.6 cm to about 5.5 cm, and an 11 gsm polyester staple fiber material. To manufacture the fluid transfer layer 92 just described, the 12 gsm spunbond material can provide a base layer while the 10 gsm wood pulp material and the 11 gsm polyester staple fiber material can be homogeneously mixed together and deposited onto the spunbond material and then hydraulically entangled with the spunbond material. In an embodiment, a wet strength agent can be included in the fluid transfer layer 92. A non-limiting example of a wet strength agent can be Kymene 6500 (557LK) or equivalent available from Ashland Inc. of Ashland, Ky., U.S.A.

In an embodiment, the fluid transfer layer 92 can be bonded with an absorbent body 46 which is made at least partially of particulate material such as superabsorbent material. In an embodiment in which the fluid transfer layer 92 at least partially or completely encompasses the absorbent body 46, the fluid transfer layer 92 should not unduly expand or stretch as this might cause particulate material to escape from the absorbent body 46. In an embodiment, the fluid transfer layer 92, while in a dry state, should have respective elongation values at peak load in the machine and cross directions of 30 percent or less and 40 percent or less. In an embodiment, the fluid transfer layer 92 may have a longitudinal length the same as the longitudinal length of the absorbent body 46.

In an embodiment, the fluid transfer layer 92 can have a basis weight less than about 40 gsm. In an embodiment, the fluid transfer layer 92 can have a basis weight less than about 40, 39, 38, 37, 36, 35, 34, 33, 32, 31, 30, 25, 20, 15, or 10 gsm. In an embodiment, the fluid transfer layer 92 can have a basis weight from about 10, 15, 20, 25, or 30 gsm to about 31, 32, 33, 34, 35, 36, 37, 38, 39, or 40 gsm Acquisition Layer:

In an embodiment, the absorbent article 10 can have an acquisition layer 94. The acquisition layer 94 can help decelerate and diffuse surges or gushes of liquid body waste penetrating the bodyside liner 40. In an embodiment, the acquisition layer 94 can be positioned between the bodyside liner 40 and the absorbent body 46 to take in and distribute urine for absorption by the absorbent body 46. In an embodiment, the acquisition layer 94 can be positioned between the bodyside liner 40 and a fluid transfer layer 92.

The acquisition layer 94 can have a wearer facing surface 144 and a garment facing surface 146. In an embodiment, the wearer facing surface 144 of the acquisition layer 94 can be bonded to the garment facing surface 150 of the bodyside liner 40. Bonding of the wearer facing surface 144 of the acquisition layer 94 to the garment facing surface 144 of the bodyside liner 40 can occur through the use of point fusion bonding. The point fusion bonding can be selected from ultrasonic bonding, pressure bonding, thermal bonding, and combinations thereof. In an embodiment, ultrasonic bonding can be utilized to point fusion bond the bodyside liner 40 to the acquisition layer 94. In an embodiment, the point fusion bonding can be provided in any pattern as deemed suitable. In an embodiment, the point fusion bonding pattern can be a pattern that provides greater than about 20 bonding points per square inch. In an embodiment, the point fusion bonding pattern can be a pattern that provides less than about 100 bonding points per square inch. In an embodiment, the point fusion bonding pattern can be a pattern that provides from about 20, 30, 40, 50, 60, 65, 66 to about 70, 80, 90 or 100 bonding points per square inch. In an embodiment, the point fusion bonding pattern can be a pattern that provides greater than about 5% bonded area. In an embodiment, the point fusion bonding pattern can be a pattern that provides less than about 30% bonded area. In an embodiment, the point fusion bonding pattern can be a pattern that provides from about 5, 6, 7, 8, 9, 10, 11, 12, 13, 14, or 15% to about 16, 17, 18, 19, 20, 21, 22, 23, 24, 25, or 30% bonded area. In an embodiment, the point fusion bonding pattern can be a pattern wherein each bonding point has an area greater than about 0.4 mm$^2$. In an embodiment, the point fusion bonding pattern can be a pattern wherein each bonding point has an area less than about 2.5 mm$^2$. In an embodiment, the point fusion bonding pattern can be a pattern wherein each bonding point has an area from about 0.4, 0.5, 0.6, 0.7, 0.8, 0.9, 0.99, 1.0, 1.1, 1.2, 1.3, 1.4, or 1.5 mm$^2$ to about 1.6, 1.7, 1.8, 1.9, 2.0, 2.1, 2.2, 2.3, 2.4, or 2.5 mm$^2$. FIGS. 6-8 provide non-limiting illustrations of point fusion bonding patterns which can bond a bodyside liner 40 to an acquisition layer 94. FIG. 6 provides a non-limiting illustration of a point fusion bonding pattern having about 40 bonding points per square inch. FIG. 7 provides a non-limiting illustration of a point fusion bonding pattern having about 66 bonding points per square inch. The bonding pattern illustrated in FIG. 7 provides for each bonding point to have an area of about 0.98 mm$^2$. FIG. 8 provides a non-limiting illustration of a point fusion bonding pattern having about 90 bonding points per square inch. Without being bound by theory, it is believed that point fusion bonding, such as, for example, via ultrasonic bonding, can reduce the amount of surface moisture on the bodyside liner 40 of the absorbent article 10. Without being bound by theory, it is believed that the use of adhesive or the use of too few bonding points to bond the acquisition layer 94 to the bodyside liner 40 can result in a higher surface moisture content on the bodyside liner 40 of the absorbent article 10 and can result in a decrease in any perceived absorbency of the absorbent article 10. Without being bound by theory, it is believed that the use of too many bonding points to bond the acquisition layer 94 to the bodyside liner 40 can increase stiffness of the absorbent article 10, can decrease resilience of the absorbent article 10, can decrease any perceived softness of the bodyside liner 40 of the absorbent article 10, and can decrease any perceived absorbency of the absorbent article 10.

The acquisition layer 94 may have any longitudinal length dimension as deemed suitable. The acquisition layer 94 may have a longitudinal length from about 120, 130, 140, 150, 160, 170, 180, 190, 200, 210, 220, 225, 230, 240, or 250 mm to about 260, 270, 280, 290, 300, 310, 320, 340, 350, 360, 380, 400, 410, 415, 420, 425, 440, 450, 460, 480, 500, 510 or 520 mm. In an embodiment, the acquisition layer 94 can have any length such that the acquisition layer 94 can be coterminous with the waist edges, 24 and 26, of the absorbent article 10. In such an embodiment in which the acquisition layer 94 can be coterminous with the waist edges, 24 and 26 of the absorbent article 10, the absorbent article 10 can be manufactured by providing a bodyside liner web and providing an acquisition layer web and bonding the two webs, the bodyside liner web and the acquisition layer web, to each other. In an embodiment, the bonding of the acquisition layer web and the bodyside liner web can occur via point fusion bonding. In such an embodiment, the point fusion bonding can be selected from ultrasonic, thermal, pressure bonding, and combination thereof. In an embodiment, the point fusion bonding can occur with a bonding pattern providing from about 20 to about 100 bond points per square inch. In an embodiment, at least one discrete absorbent body 46 can be provided and superposed on the combination of the bodyside liner web and the acquisition layer web. In an embodiment, a series of discrete absorbent bodies 46 can be provided and superposed on the combination of the bodyside liner web and the acquisition layer web. In an embodiment, a backsheet layer web can be provided and superposed on the absorbent body 46. The backsheet layer web can be bonded to the combination bodyside liner web and acquisition layer web to form at least one absorbent composite. In an embodiment in which a series of absorbent bodies have been provided, a series of absorbent composites can be formed with the bonding of the backsheet layer web to the combination bodyside liner web and acquisition layer web. In an embodiment, an absorbent composite can be separated from a successive absorbent composite to form a discrete absorbent article 10. In an embodiment, a fluid transfer layer web can be provided. In such an embodiment, the fluid transfer layer web can be positioned between the acquisition layer web and the at least one absorbent body 46.

In an embodiment, the fluid transfer layer web can partially or completely encompass the at least one absorbent body 46. In an embodiment, the fluid transfer layer web can be bonded with the acquisition layer web. In such an embodiment, the bonding of the fluid transfer layer web to the acquisition layer web can occur via adhesive.

In an embodiment, the longitudinal length of the acquisition layer 94 can be the same as the longitudinal length of the absorbent body 46. In such an embodiment the midpoint of the longitudinal length of the acquisition layer 94 can substantially align with the midpoint of the longitudinal length of the absorbent body 46.

In an embodiment, the longitudinal length of the acquisition layer 94 can be shorter than the longitudinal length of the absorbent body 46. In such an embodiment, the acquisition layer 94 may be positioned at any desired location along the longitudinal length of the absorbent body 46. As an example of such an embodiment, the absorbent article 10 may contain a target area 152 where repeated liquid surges typically occur in the absorbent article 10. The particular location of a target area 152 can vary depending on the age and gender of the wearer of the absorbent article 10. For example, males tend to urinate further toward the front end of the absorbent article 10 and the target area 152 may be phased forward within the absorbent article 10. For example, the target area 152 for a male wearer may be positioned about 2¾" forward of the midpoint of the absorbent body 46 and may have a length of about ±3" and a width of about ±2". The female target area 152 can be located closer to the center of the crotch region 18 of the absorbent article 10. For example, the target area 152 for a female wearer may be positioned about 1" forward of the midpoint of the absorbent body 46 and may have a length of about ±3" and a width of about ±2". As a result, the relative longitudinal placement of the acquisition layer 94 within the absorbent article 10 can be selected to best correspond with the actual target area 152 of either or both categories of wearers. In an embodiment, the absorbent article 10 may contain a target area 152 centered within the crotch region 18 of the absorbent article 10 with the premise that the absorbent article 10 would be worn by a female wearer. The acquisition layer 94, therefore, may be positioned along the longitudinal length of the absorbent article 10 such that the acquisition layer 94 is substantially aligned with the target area 152 of the absorbent article 10 intended for a female wearer. Alternatively, the absorbent article 10 may contain a target area 152 positioned between the crotch region 18 and the front waist region 12 of the absorbent article 10 with the premise that the absorbent article 10 would be worn by a male wearer. The acquisition layer 94, therefore, may be positioned along the longitudinal length of the absorbent article 10 such that the acquisition layer 94 is substantially aligned with the target area 152 of the absorbent article 10 intended for a male wearer. Referring to FIG. 9, in an embodiment, the bodyside liner 40 can be bonded, via point fusion bonding, to the acquisition layer 94 at least partially in the target area 152 of the absorbent article 10. The point fusion bonding can result in bond points 154 in the bonded area. In an embodiment, the acquisition layer 94 can have a size dimension that is the same size dimension as the target area 152 of the absorbent article 10 or a size dimension greater than the size dimension of the target area 152 of the absorbent article 10. In an embodiment, the acquisition layer 94 can be bonded, via point fusion bonding, to the bodyside liner 40 at least partially in the target area 152 of the absorbent article 10. In an embodiment in which the acquisition layer 94 has a size dimension greater than a size dimension of the target area 152 of the absorbent article 10, the acquisition layer 94 need not be bonded to the bodyside liner 40 in any location outside the size dimension of the target area 152 of the absorbent article 10. In an embodiment, the bodyside liner 40 can be bonded to the acquisition layer 94, via point fusion bonding, at least partially in the target area 152 of the absorbent article 10 and at least partially in at least one area(s) of the absorbent article 10 outside of the target area 152 of the absorbent article 10. In such an embodiment, the acquisition layer 94 can be positioned such that it covers the target area 152 of the absorbent article 10 and can have a size dimension larger than the target area 152 of the absorbent article 10. In such an embodiment, the acquisition layer 94 can be bonded, such as via point fusion bonding, to the bodyside liner 40 in a location that covers the target area 152 of the absorbent article 10 and in at least one location(s) beyond the target area 152 of the absorbent article 10.

In various embodiments, the acquisition layer 94 can have a longitudinal length shorter than the longitudinal length of the absorbent body 46. In an embodiment in which the absorbent article 10 is a diaper, the acquisition layer 94 may have a longitudinal length from about 120, 130, 140, 150, 160, 170, or 180 mm to about 200, 210, 220, 225, 240, 260, 280, 300, 310 or 320 mm. In such an embodiment, the acquisition layer 94 may be shorter in longitudinal length than the longitudinal length of the absorbent body 46 and may be phased from the front end edge 52 of the absorbent body 46 a distance of from about 15, 20, or 25 mm to about 30, or 40 mm. In an embodiment in which the absorbent article 10 may be a training pant or youth pant, the acquisition layer 94 may have a longitudinal length from about 120, 130, 140, 150, 200, 210, 220, 230, 240 or 250 mm to about 260, 270, 280, 290, 300, 340, 360, 400, 410, 420, 440, 450, 460, 480, 500, 510 or 520 mm. In such an embodiment, the acquisition layer 94 may have a longitudinal length shorter than the longitudinal length of the absorbent body 46 and may be phased a distance of from about 25, 30, 35 or 40 mm to about 45, 50, 55, 60, 65, 70, 75, 80 or 85 mm from the front end edge 52 of the absorbent body 46. In an embodiment in which the absorbent article 10 is an adult incontinence garment, the acquisition layer 94 may have a longitudinal length from about 200, 210, 220, 230, 240, or 250 mm to about 260, 270, 280, 290, 300, 320, 340, 360, 380, 400, 410, 415, 425, or 450 mm. In such an embodiment, the acquisition layer 94 may have a longitudinal length shorter than the longitudinal length of the absorbent body 46 and the acquisition layer 94 may be phased a distance of from about 20, 25, 30 or 35 mm to about 40, 45, 50, 55, 60, 65, 70 or 75 mm from the front end edge 52 of the absorbent body 46.

The acquisition layer 94 may have any width as desired. The acquisition layer 94 may have a width dimension from about 15, 20, 25, 30, 35, 40, 45, 50, 55, 60, or 70 mm to about 80, 90, 100, 110, 115, 120, 130, 140, 150, 160, 170, or 180 mm. The width of the acquisition layer 94 may vary dependent upon the size and shape of the absorbent article 10 within which the acquisition layer 94 will be placed. The acquisition layer 94 can have a width smaller than, the same as, or larger than the width of the absorbent body 46. Within the crotch region 16 of the absorbent article 10, the acquisition layer 94 can have a width smaller than, the same as, or larger than the width of the absorbent body 46.

In an embodiment, the acquisition layer 94 can be a through-air bonded-carded web such as a 35 gsm through-air bonded-carded web composite composed of a homogeneous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite composed of about 35% Huvis 180-N (PE/PP 6d), about 35% Huvis N-215 (PE/PP 2d), and about 30% Huvis SD-10 PET 6d, or equivalent composite, available from SamBo Company, Ltd, Korea.

The acquisition layer 94 may have additional parameters including basis weight and thickness. In an embodiment, the basis weight of the acquisition layer 94 can be at least about 20 gsm. In an embodiment, the basis weight of the acquisition layer 94 can be from about 20, 30, 40, 50 or 60 gsm to about 65, 70, 75, 80, 85, 90, 100 gsm. In an embodiment, the basis weight of the acquisition layer 94 can be less than about 100, 90, 85, 80, 75, 70, 65, 60 or 50 gsm. In an embodiment, the acquisition layer 94 can have a thickness, measured at 0.05 psi, of less than about 1.5 mm. In an embodiment, the acquisition layer 94 can have a thickness, measured at 0.05 psi, of less than about 1.5, 1.25, or 1.0 mm.

In an embodiment, the acquisition layer 94 can be bonded to the fluid transfer layer 92 using a suitable adhesive. In an embodiment, the acquisition layer 94 can be point fusion bonded to the bodyside liner 40 and can be adhesively bonded to the fluid transfer layer 92.

Bodyside Liner:

The bodyside liner 40 of the absorbent article 10 can overlay the absorbent body 46 and the outer cover 38 and can isolate the wearer's skin from liquid waste retained by the absorbent body 46. As described herein, the bodyside liner 40 may also overlay an acquisition layer 94 and may be bonded to the acquisition layer 94, such as by a point fusion bonding. The point fusion bonding may be selected from ultrasonic, thermal, pressure bonding, and combinations thereof. In an embodiment, the bodyside liner 40 can be bonded to the acquisition layer 94 utilizing ultrasonic bonding. In an embodiment, the bodyside liner 40 can extend beyond the absorbent body 46 and/or the acquisition layer 94 to overlay a portion of the inner layer 80 of the outer cover 38 and can be bonded thereto by any method deemed suitable, such as, for example, by being bonded thereto by adhesive, to substantially enclose the absorbent body 46 between the outer cover 38 and the bodyside liner 40. The bodyside liner 40 may be slightly narrower than the outer cover 38, but it is to be understood that the bodyside liner 40 and the outer cover 38 may be of the same dimensions. It is also contemplated that the bodyside liner 40 may not extend beyond the absorbent body 46 and may not be secured to the outer cover 38. The bodyside liner 40 can be suitably compliant, soft feeling, and non-irritating to the wearer's skin and can be less hydrophilic than the absorbent body 46 to provide a relatively dry surface to the wearer and permit liquid body waste to readily penetrate through its thickness.

The bodyside liner 40 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the bodyside liner 40. For example, the bodyside liner 40 can be composed of a meltblown or spunbond web of polyolefin fibers. Alternatively, the bodyside liner 40 can be a bonded-carded web composed of natural and/or synthetic fibers. The bodyside liner 40 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 40 or it can be selectively applied to particular sections of the bodyside liner 40.

In an embodiment, a bodyside liner 40 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 40 can be a 12 gsm spunbond-meltblown-spunbond substrate having 10% meltblown content applied between the two spunbond layers. In an embodiment, a bodyside liner 40 can be a 20 gsm through-air bonded-carded web having about 50% Haesung HP-120 FD 2 denier and about 50% Huvis SD 1.5 denier fibers as available from Korea Vilene Co., Ltd, Korea. In such an embodiment, the fibers can be homogeneously mixed. In an embodiment, a bodyside liner 40 can be a 20 gsm through-air bonded-carded web having about 50% Haesung HP-120 FD 2 denier fibers and about 50% Huvis SD 1.5 denier fibers as available from SamBo Co., Ltd, Korea. In such an embodiment, the bodyside liner 40 can be layered such that a first layer is substantially composed of the 2 denier fibers and the other layer is substantially composed of the 1.5 denier fibers. In such an embodiment, the layer having the 2 denier fibers may be a wearer facing layer and the layer having the 1.5 denier fibers may be a garment facing layer. In such an embodiment, the 2 denier fiber layer can provide a soft feeling to the body of the wearer and the 1.5 denier fiber layer can be in contact with the acquisition layer 94 of the absorbent article 10.

In an embodiment, the bodyside liner 40 can have a basis weight less than about 30 gsm. In an embodiment, the bodyside liner 40 can have a basis weight less than about 30, 28, 26, 24, 22, 20, 18, 16, 14 or 12 gsm. In an embodiment, the bodyside liner 40 can have a basis weight from about 6, 8, 10, 12, 14, 16, or 18 gsm to about 20, 22, 24, 26, 28 or 30 gsm.

Although the outer cover 38 and bodyside liner 40 can include elastomeric materials, it is contemplated that the outer cover 38, the bodyside liner 40 and the absorbent body 46 can be composed of materials which are generally non-elastomeric. In an embodiment, the bodyside liner 40 can be stretchable, and more suitably elastic. In an embodiment, the bodyside liner 40 can be suitably stretchable and more suitably elastic in at least the lateral or circumferential direction of the absorbent article 10. In other aspects, the bodyside liner 40 can be stretchable, and more suitably elastic, in both the lateral and the longitudinal directions.

In an embodiment, the fluid transfer layer 92, the acquisition layer 94 and the bodyside liner 40 can have a combined basis weight of less than about 150 gsm. In an embodiment, the fluid transfer layer 92, the acquisition layer 94 and the bodyside liner 40 can have a combined basis weight of less than about 150, 145, 140, 135, 130, 125, 120, 115, 110, 105, 100, 95, 90, 85, 80 or 75 gsm. In an embodiment, the fluid transfer layer 92, the acquisition layer 94, and the bodyside liner 40 can have a combined basis weight from about 75, 80, 85, 90, 95, or 100 gsm to about 105, 110, 115, 120, 125, 130, 135, 140, 145 or 150 gsm. In an embodiment, the fluid transfer layer 92 can have a basis weight from about 10, 15, 20, 25, or 30 gsm to about 31, 32, 33, 34, 35, 36, 37, 38, 39, or 40 gsm, the acquisition layer 94 can have a basis weight from about 20, 30, 40, 50 or 60 gsm to about 65, 70, 75, 80, 85, 90 or 100 gsm, and the bodyside liner 40 can have a basis weight from about 6, 8, 10, 12, 14, 16 or 18 gsm to about 20, 22, 24, 26, 28 or 30 gsm.

Containment Flaps:

Containment flaps, 56 and 58, can be secured to the bodyside liner 40 in a generally parallel, spaced relation with each other laterally inward of the leg openings, 62 and 64, to provide a barrier against the flow of urine to the leg openings, 62 and 64. The containment flaps, 56 and 58, can extend longitudinally from the front waist region 12 of the absorbent article 10, through the crotch region 16 to the back waist region 14 of the absorbent article 10. Each containment flap, 56 and 58, can have a non-woven layer 96 and a film layer 98 bonded to the non-woven layer 96, such as by being bonded thereto by adhesive 100. Flap elastics, 66 and 68, can be secured by suitable adhesive 102 between the non-woven layer 96 and the film layer 98, generally at a distal end 104 of the containment flaps, 56 and 58, with the non-woven layer 96 being folded over the flap elastics, 66 and 68, and the film layer 98 at the distal end 104. The containment flaps, 56 and 58, can be bonded to the bodyside liner 40 by a seam of adhesive 106 to define a proximal end 108 of the containment flaps, 56 and 58.

The flap elastics, 66 and 68, as illustrated, can have two strands of elastomeric material extending longitudinally along the distal ends 104 of the containment flaps, 56 and 58, in generally parallel, spaced relation with each other. The elastic strands can be secured between the non-woven layer 96 and the film layer 98 while in an elastically contractible condition such that contraction of the strands gathers and shortens the distal ends 104 of the containment flaps, 56 and 58. As a result, the elastic strands can bias the distal ends 104 of each containment flap, 56 and 58, toward a position spaced from the proximal end 108 of the containment flaps, 56 and 58, so that the containment flaps, 56 and 58, can extend away from the bodyside liner 40 in a generally upright orientation of the containment flaps, 56 and 58, especially in the crotch region 16 of the absorbent article 10, when the absorbent article 10 is fitted on the wearer. It is to be understood, however, that the containment flaps, 56 and 58, may be omitted from the absorbent article 10 without departing from the scope of this disclosure.

Leg Elastics:

Leg elastic members, 74 and 76, can be secured between the outer and inner layers, 78 and 80, respectively, of the outer cover 38, such as by being bonded therebetween by a laminate adhesive 82, generally adjacent lateral outer edges, 110 and 112, of the inner layer 80 of the outer cover 38. Alternatively, the leg elastic members, 74 and 76, may be disposed between other layers of the absorbent article 10. A wide variety of elastic materials may be used for the leg elastic members, 74 and 76. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

Fastening System:

In an embodiment, the absorbent article 10 can include a fastener system. The fastener system can include one or more back fasteners 114 and one or more front fasteners 116. Portions of the fastener system may be included in the front waist region 12, back waist region 14, or both. The fastener system can be configured to secure the absorbent article 10 about the waist of the wearer and maintain the absorbent article 10 in place during use. In an embodiment, the back fasteners 114 can include one or more materials bonded together to form a composite ear as is known in the art. For example, the composite fastener may be composed of a stretch component 118, a nonwoven carrier or hook base 120, and a fastening component 122.

Waist Elastic Members:

In an embodiment, the absorbent article 10 can have waist elastic members, 70 and 72, which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 70 and 72, may be omitted from the absorbent article 10 without departing from the scope of this disclosure.

Side Panels:

In an embodiment in which the absorbent article 10 can be a training pant, youth pant, diaper pant, or adult absorbent pant, the absorbent article 10 may have front side panels, 124 and 126, and rear side panels, 128 and 130. FIG. 10 provides a non-limiting illustration of an absorbent article 10 that can have side panels, such as front side panels, 124 and 126, and rear side panels, 128 and 130. The front side panels 124 and 126 and the rear side panels 128 and 130 of the absorbent article 10 can be bonded to the absorbent article 10 in the respective front and back waist regions, 12 and 14, and can extend outwardly beyond the longitudinal side edges, 20 and 22, of the absorbent article 10. In an example, the front side panels, 124 and 126, can be bonded to the inner layer 80 of the outer cover 38, such as being bonded thereto by adhesive, by pressure bonding, by thermal bonding or by ultrasonic bonding. These side panels, 124 and 126, may also be bonded to the outer layer 78 of the outer cover 38, such as by being bonded thereto by adhesive, by pressure bonding, by thermal bonding, or by ultrasonic bonding. The back side panels, 128 and 130, may be secured to the outer and inner layers, 78 and 80 respectively, of the outer cover 38 at the back waist region 14 of the absorbent article 10 in substantially the same manner as the front side panels, 124 and 126. Alternatively, the front side panels, 124 and 126, and the back side panels, 128 and 130, may be formed integrally with the absorbent article 10, such as by being formed integrally with the outer cover 38, the bodyside liner 40 or other layers of the absorbent article 10.

For improved fit and appearance, the front side panels, 124 and 126, and the back side panels, 128 and 130, can suitably have an average length measured parallel to the longitudinal axis of the absorbent article 10 that is about 20 percent or greater, and more suitably about 25 percent or greater, of the overall length of the absorbent article 10, also measured parallel to the longitudinal axis. For example, absorbent articles 10 having an overall length of about 54 centimeters, the front side panels, 124 and 126, and the back side panels, 128 and 130, suitably have an average length of about 10 centimeters or greater, and more suitably have an average length of about 15 centimeters. Each of the front side panels, 124 and 126, and back side panels, 128 and 130, can be constructed of one or more individual, distinct pieces of material. For example, each front side panel, 124 and 126, and back side panel, 128 and 130, can include first and second side panel portions (not shown) joined at a seam (not shown), with at least one of the portions including an elastomeric material. Alternatively, each individual front side panel, 124 and 126, and back side panel, 128 and 130, can be constructed of a single piece of material folded over upon itself along an intermediate fold line (not shown).

The front side panels, 124 and 126, and back side panels, 128 and 130, can each have an outer edge 132 spaced laterally from the engagement seam 134, a leg end edge 136 disposed toward the longitudinal center of the absorbent article 10, and a waist end edge 138 disposed toward a longitudinal end of the absorbent article 10. The leg end edge 136 and waist end edge 138 can extend from the longitudinal side edges, 20 and 22, of the absorbent article 10 to the outer edges 132. The leg end edges 136 of the front side panels, 124 and 126, and back side panels, 128 and 130, can form part of the longitudinal side edges, 20 and 22, of the absorbent article 10. The leg end edges 136 of the illustrated absorbent article 10 can be curved and/or angled relative to the transverse axis to provide a better fit around the wearer's legs. However, it is understood that only one of the leg end edges 136 can be curved or angled, such as the leg end edge 136 of the back waist region 14, or neither of the leg end edges 136 can be curved or angled, without departing from the scope of this disclosure. The waist end edges 138 can be parallel to the transverse axis. The waist end edges 138 of the front side panels, 124 and 126, can form part of the front waist edge 24 of the absorbent article 10, and the waist end edges 138 of the back side panels, 128 and 130, can form part of the back waist edge 26 of the absorbent article 10.

The front side panels, 124 and 126, and back side panels, 128 and 130, can include an elastic material capable of stretching laterally. Suitable elastic materials, as well as one described process for incorporating elastic front side panels, 124 and 126, and back side panels, 128 and 130, into an absorbent article 10 are described in the following U.S. Pat. No. 4,940,464 issued Jul. 10, 1990 to Van Gompel et al., U.S. Pat. No. 5,224,405 issued Jul. 6, 1993 to Pohjola, U.S. Pat. No. 5,104,116 issued Apr. 14, 1992 to Pohjola, and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., and PCT Application WO 01/88245 in the name of Welch et al., all of which are incorporated herein by reference. Other suitable materials are described in U.S. patent application Ser. No. 12/649,508 to Welch et al. and Ser. No. 12/023,447 to Lake et al., all of which are incorporated herein by reference. Alternatively, the front side panels, 124 and 126, and back side panels, 128 and 130, may include other woven or nonwoven materials, such as those described above as being suitable for the outer cover 38 or bodyside liner 40, mechanically pre-strained composites, or stretchable but inelastic materials.

Non-Limiting Examples of Embodiments of an Absorbent Article:

In an embodiment, an absorbent article 10 can have an outer cover 38, an absorbent body 46, a fluid transfer layer 92, an acquisition layer 94 and a bodyside liner 40. In such an embodiment, the bodyside liner 40 can be composed of a 12 gsm spunbond-meltblown-spunbond substrate having 10% meltblown content applied between the two spunbond layers. In such an embodiment, the acquisition layer 94 can be composed of a through-air bonded carded web such as a 35 gsm through-air bonded carded web composite composed of a homogeneous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite composed of about 35% Huvis 180-N (PE/PP 6d), about 35% Huvis N-215 (PE/PP 2d), and about 30% Huvis SD-10 PET 6d or equivalent available from SamBo Company, Ltd, Korea. In such an embodiment, the fluid transfer layer 92 can be a 10 gsm spunbond-meltblown-spunbond material.

In an embodiment, an absorbent article 10 can have an outer cover 38, an absorbent body 46, a fluid transfer layer 92, an acquisition layer 94 and a bodyside liner 40. In such an embodiment, the bodyside liner 40 can be composed of a 12 gsm spunbond-meltblown-spunbond substrate having 10% meltblown content applied between the two spunbond layers. In such an embodiment, the acquisition layer 94 can be composed of a through-air bonded carded web such as a 35 gsm through-air bonded carded web composite composed of a homogeneous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite composed of about 35% Huvis 180-N (PE/PP 6d), about 35% Huvis N-215 (PE/PP 2d), and about 30% Huvis SD-10 PET 6d or equivalent available from SamBo Company, Ltd, Korea. In such an embodiment, the fluid transfer layer 92 can be composed of at least one material which has been hydraulically entangled into a nonwoven substrate. A non-limiting example of a fluid transfer layer 92 can be a 33 gsm hydraulically entangled substrate. In such an example, the fluid transfer layer 92 can be a 33 gsm hydraulically entangled substrate composed of a 12 gsm spunbond material, a 10 gsm pulp material, and an 11 gsm polyester staple fiber material. In such an embodiment, a wet strength agent can be included in the fluid transfer layer 92. A non-limiting example of a wet strength agent can be Kymene 6500 (557LK) from Ashland Inc. of Ashland, Ky., U.S.A.

In an embodiment, an absorbent article 10 can have an outer cover 38, an absorbent body 46, a fluid transfer layer 92, an acquisition layer 94 and a bodyside liner 40. In such an embodiment, a bodyside liner 40 can be a 20 gsm through-air bonded-carded web having about 50% Haesung HP-120 FD 2 denier and about 50% Huvis SD 1.5 denier fibers as available from Korea Vilene Co., Ltd, Korea. In such an embodiment, the fibers can be homogeneously mixed or the bodyside liner 40 can be layered such that a first layer is substantially composed of the 2 denier fibers and the other layer is substantially composed of the 1.5 denier fibers. In such an embodiment in which the bodyside liner 40 is layered, the layer having the 2 denier fibers may be in contact with the body and the layer having the 1.5 denier fibers may be in contact with the acquisition layer 94 of the absorbent article 10. In such an embodiment, the acquisition layer 94 can be composed of a through-air bonded carded web such as a 35 gsm through-air bonded carded web composite composed of a homogeneous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite composed of about 35% Huvis 180-N (PE/PP 6d), about 35% Huvis N-215 (PE/PP 2d), and about 30% Huvis SD-10 PET 6d or equivalent available from SamBo Company, Ltd, Korea. In such an embodiment, the fluid transfer layer 92 can be a 10 gsm spunbond-meltblown-spunbond material.

Experiments:

For the experiments listed below, the following table of Material Descriptions applies:

TABLE 1

| Material Descriptions: | |
| --- | --- |
| Material Code | Material Description |
| A | Bodyside Liner: A 20 gsm through-air bonded-carded web composed of about 50% of Haesung HP-120 FD 2 d fibers on the skin contact side of the web and about 50% Huvis SD 1.5 d fibers on the non-skin contact side of the web. The web has a thickness of 0.60 mm when measured under a pressure of 0.345 kPa. The web is available from SamBo Co., Ltd., Korea. |

TABLE 1-continued

Material Descriptions:

| Material Code | Material Description |
|---|---|
| B | Bodyside Liner: A 12 gsm white wettable spunbond-meltblown-spunbond web with the spunbond layers composed of 12 gsm random laid continuous polypropylene round filaments and the meltblown layer composed of 10% (1.2 gsm) meltblown fibers. The web is made wettable with up to about 2% of a 3:1 ratio of Cirrasol PP862/Standapol 215 UP using a foaming system. |
| C | Acquisition Layer: A 55 gsm through-air bonded-carded web composed of homogeneous blend of 40% FiberVisions 7 denier ESC 236 hollow polypropylene fibers and 60% FiberVisions 3 denier T-118 bicomponent fibers. The web has a thickness of 0.62 mm when measured under a pressure of 0.345 kPa. The fibers are available from FiberVisions Corp., Duluth, GA, U.S.A. |
| D | Acquisition Layer: A 129 gsm through-air bonded-carded web composed of a homogeneous blend of 40% FiberVisions 7 denier ESC 236 hollow polypropylene fibers and 60% FiberVisions 6 denier T-118 bicomponent fibers. The web has a thickness of 1.4 mm when measured under a pressure of 0.345 kPa. The fibers are available from FiberVisions Corp., Duluth, GA, U.S.A. |
| E | Acquisition Layer: A 68 gsm through-air bonded-carded web composed of a homogeneous mixture of 40% INVISTA T295 6 denier polyester fibers and 60% FiberVisions 3 denier bicomponent fibers. The web has a thickness of 0.77 mm when measured under 0.345 kPa. FiberVisions Corp. is located in Duluth, GA, U.S.A. and the INVISTA fibers are available from Auriga Polymers, Inc. located in Charlotte, NC, U.S.A. |
| F | Acquisition Layer: A 150 gsm through-air bonded-carded web composed of a homogeneous mixture of 40% INVISTA 6 d polyester fibers and 60% FiberVisions ESC 236 6 d denier bicomponent fibers. The web has a thickness of 1.42 mm when measured under a pressure of 0.345 kPa. FiberVisions Corp. is located in Duluth, GA, U.S.A. and the INVISTA fibers are available from Auriga Polymers, Inc. located in Charlotte, NC, U.S.A. |
| G | Acquisition Layer: A 200 gsm through-air bonded-carded web composed of a homogeneous mixture of 40% INVISTA 6 d polyester fibers and 60% FiberVisions ESC 236 6 d bicomponent fibers. The web has a thickness of 1.89 mm when measured under a pressure of 0.345 kPa. FiberVisions Corp. is located in Duluth, GA, U.S.A. and the INVISTA fibers are available from Auriga Polymers, Inc. located in Charlotte, NC, U.S.A. |
| H | Acquisition Layer: A 35 gsm through-air bonded-carded web composite composed of a homogeneous mixture of about 35% Huvis N-189 (PE/PP 6d) fibers, about 35% Huvis N-215 (PE/PP 2 d) fibers and about 30% Huvis SD-10 PET 6 d fibers. The material has a thickness of 1.1 mm when measured under a pressure of 0.345 kPa. The web is available from Korea Vilene Co., Ltd., Korea. |
| I | Fluid Transfer Layer: A Avgol SMS 10 gsm Multicolor Phillic Barrier Layer composed of a spunbond-meltblown-spunbond web having about 2.0 gsm meltblown content available from Avgol Nonwovens Industries, Mocksville, NC, U.S.A. |
| J | Fluid Transfer Layer: A 33 gsm layered spunlace material composed of an 11 gsm spunbonded polypropylene layer and a homogeneous 22 gsm hydraulically entangled (on the spunbond material) layer composed of about 48% *Radiata* Pine pulp supplied by J. Carter Holt Harvey Pulp and Paper and about 52% 6d polyester fibers supplied by Huvis. This material has a caliper of 0.27 mm when measured under a pressure of 0.345 kPa. |
| K | Fluid Transfer Layer: A white 16.6 gsm 100% elemental chlorine free, single ply, low porosity creped wadding, water-cut-on-machine. This material is available from Cellu Tissue - Natural Dam, Gouverneur, N.Y., U.S.A. |

For experiments 1-4 listed below, absorbent composites were handmade according to the following assembly method:

Assembly Instructions for Absorbent Composites

Materials:

Film: Berry Plastics XP-8695H Inner Cover Film available from Berry Plastics, Washington, Ga., USA.

Absorbent body, bodyside liner, acquisition layer, and fluid transfer layer are unique to each experiment or code and specific materials are noted for each experimental code.

Construction Adhesive: H2525A available from Bostik Inc., U.S.A.

Construction Adhesive Glue Gun Nozzle: unibody spray nozzle with a 0.012 inch orifice diameter as available as manufacturing part No. 152168 from Nordson Corp., U.S.A.

Material Preparation:

1. Film: Cut to a minimum size of 16 inches long by 6.5 inches wide.

2. Fluid Transfer Layer: Cut to 16 inches long by 4 inches wide.

3. Acquisition Layer: Cut to 16 inches long by 4.5 inches wide.

4. Bodyside Liner: Cut to a minimum of 16 inches long by 6.5 inches wide.

Assembly Instructions:

1. Bond the acquisition layer to the bodyside liner using the method specified for each experimental code which can be found within each experiment described below. The acquisition layer and bodyside liner should be equal in length and aligned on the midline of the width.

2. Attach the absorbent body, centered in both the length and width directions, to the film using 15 gsm of construction adhesive to attach the backing sheet of the absorbent body to the film.

3. Attach the fluid transfer layer to the absorbent body using 11 gsm of construction adhesive. The midline of the width of the fluid transfer layer should align with the midline of the width of the absorbent body.
4. Apply 17.5 gsm of construction adhesive to the entire exposed surface of the absorbent composite constructed so far, which may include exposed film, absorbent body components, and/or the fluid transfer layer.
5. Attach the acquisition layer (which is already bonded to the bodyside liner) to the fluid transfer layer. The acquisition layer and fluid transfer layer should be equal in length and aligned on the midline of the width. Smooth out any wrinkles in the bodyside liner and ensure that it is tacked down to any adhesive not covered by the acquisition layer.
6. Ensure that all the materials are adhered into place by pressing firmly on the perimeter 1.5 inches.
7. Cut out the assembled absorbent composite. Finished size should be 6 inches wide by 15.5 inches long.

For the experiments listed below, the following Surface Moisture Test Method was followed:

Surface Moisture Test Method:

The Surface Moisture Test Method is used to measure the intake time and surface moisture after insult of an absorbent article or absorbent composite. The intake time is measured using a stopwatch and visually estimating the length of time required to intake a single insult of testing fluid. A layer of blotter paper is placed under the test specimen to collect and quantify any testing fluid that may flow over the side of the test specimen. The surface moisture is measured by quantifying the amount of testing fluid that emerges from the body side of the test specimen after insult.

Figure 13A:
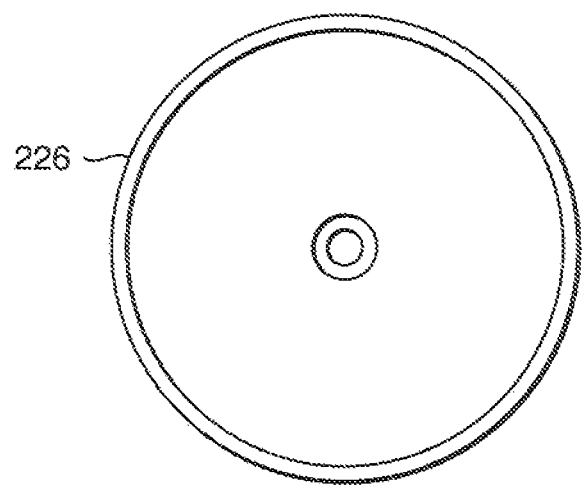
FIG. 13A and FIG. 13B are a top view and a side view, respectively, of a funnel employed in surface moisture testing.
Figure 13B:
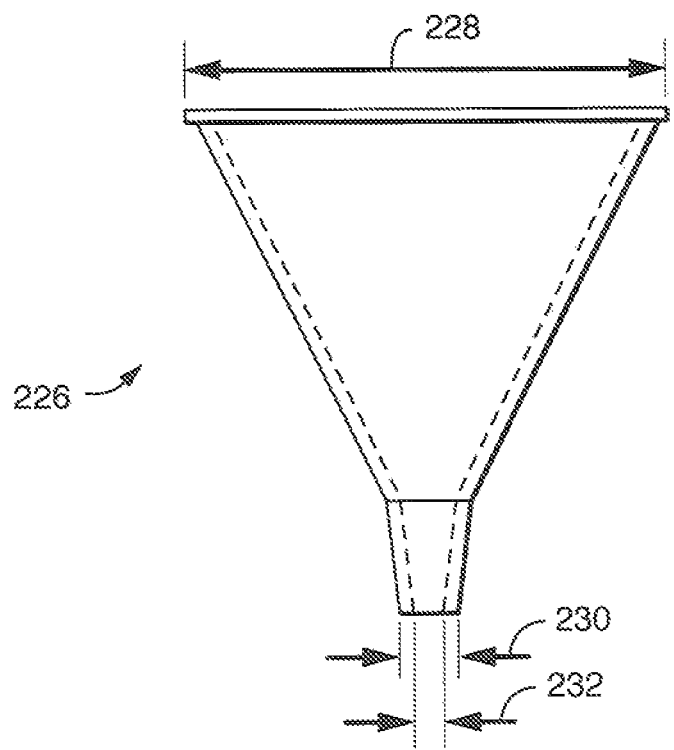

Preparation of Apparatus:
1. Surface Moisture Boards: Refer to FIGS. 11A-11B and 12A-12B. As representatively shown in FIGS. 11A and 11B, bottom board 200 includes a rectangular shaped base member 202 and a smaller, rectangular shaped platform member 204. The base member 202 has an overall length (top to bottom of the figure) of 14 in., an overall side-to-side width of 8 in. and a thickness of 0.34 in. Platform member 204 has a length of 6 in, a width of 4 in., and a thickness of 0.22 in. The platform member 204 is centered onto the top of base member 202 and secured in place, such as by adhesive bonding. The four, peripheral top edges of platform member 204 are shaped with a 0.05 inch by 45° chamfer. Rectangular base member 202 includes a pair of 0.5 inch diameter, cylindrical rods 206 which are press fitted into mating holes and secured in place with suitable attachment means, such as adhesive bonding. The center of each cylindrical rod 206 is positioned 0.75 in. from the top, end edge of the base member 202 and 0.75 in. from the immediately adjacent side edge of the base member 202. The cylindrical rods 206 extend about 1.63 in. above the surface of the base member 202, and the uppermost exposed edges of the cylindrical rods 206 are rounded with a contour radius of about 0.16 inches. A series of four reference lines 208 are scribed into the top surface of base member 202 and extend laterally across the width of the base member 202. The scribe lines are parallel and spaced from the top, end edge of base member 202 by distances of 1.25 in., 1.50 in., 2.00 in., and 3 in., respectively. The components of bottom board 200 are composed of a suitable water resistant material, such as Lexan plastic. Top board 210 includes a top plate 212 and cylindrical tube 214 which extends generally perpendicular from the plane defined by uppermost, top surface of the top plate 212. Top plate 212 is generally rectangular in shape and is sized with substantially the same length, width and thickness as bottom board 200. The top plate 212 includes a pair of 0.53 in. diameter through holes 216 which are located adjacent the top edge of top plate 212 and configured to slip over cylindrical rods 206 in bottom board 200 to appropriately locate top board 210 in a substantially congruent, coextensive position over bottom board 200. A series of four reference lines 218 are inscribed into a top surface of top plate 212 and extend linearly in the transverse direction across the width of top plate 212. The scribe lines are parallel and spaced from the top, end edge of top plate 212 by distances of 1.25 in., 1.50 in., 2.00 in., and 3 in., respectively. The medial section of top plate 212 includes a circular hole 220 which is sized to accept the place of cylindrical tube 214. Cylindrical tube 214 has a 2.5 inch outside diameter, a 2.0 inch inside diameter and an overall length of 3.75 inch. The cylindrical tube 214 is press fitted and attached in place within the circular hole 220 by suitable attachment means, such as adhesive bonding. Circular hole 220 is centered with respect to both the length and width of the top plate 212. Cylindrical tube 214 projects generally perpendicular from the top surface 222 of top plate 212 and extends through the thickness of the top plate 212 to protrude a small distance of about 0.03 inches past the bottom surface 224 of top plate 212. The upper, entrance edge of cylindrical tube 214 has an internal chamfer which generally matches the conical shape of the associated funnel representatively shown in FIGS. 13A and 13B. Similar to the components of bottom board 200, the components of top plate 212 are composed of a suitable water resistant material, such as Lexan plastic.
2. Four ounce Funnel: Refer to FIGS. 13A and 13B. Funnel has inlet diameter 228 of 3.25 inch, a funnel throat diameter 230 of 0.438 inch, and a spout outlet diameter 232 of 0.25 inch. The given measurements are inside diameters.
3. Dispensing System: Masterflex Digi-Staltic automatic dispensing system, 120-230 VAC switchable, with anti-drip feature; includes pump, pump head and controller. The insult amount is set to 70 mL and the delivery rate is set to 7.5 mL/second. An example is a Cole-Parmer Instrument Company, part number 77340-00, or equivalent.
4. Balance: accurate to 0.001 grams and fully-enclosed to prevent excessive fluctuations in measurements.
5. Testing Liquid: FD&C Blue No. 1 dye, such as CI 42090 Brilliant Blue FCF, available from Hilton Davis Co. of Cincinnati, Ohio. Prepare blue dye concentrate by dissolving approximately four grams of FD&C Blue in 250 mL deionized water and filtering through a Corning® 250 mL Filter System. Prepare Testing Liquid by adding 4 mL of blue dye concentrate to 1 L of saline.
6. Blotter Paper: Verigood grade, white, 100 lb, 475 by 600 mm (19 by 24 inch) long stock, 250 sheets per ream, cut to a specified size of 88 by 300 mm (3.5 by 12 inches) or equivalent, available from Schabo Printing, Black Creek, Wis., U.S.A.
7. A non-permeable, non-flexible clear board of a suitable water resistant material, such as Lexan, cut to 114 by 432 mm (4.5 by 17 inches) and weighing 177.073 grams.
8. Stopwatch: Readable to 0.01 second; example: VWR Scientific Products part number 62379-218, or equivalent 9. Timer: Readable to 1 second; example: 3-channel alarm timer, VWR Scientific Products part number 62344-600, or equivalent 10. Testing is in a controlled laboratory environment: 23±2° C. (73.4±3.6° F.) and 50±5% relative humidity.

Specimen Preparation for Absorbent Articles, Such as Diapers
1. Use scissors to cut the leg elastics off of the absorbent article; cut between the edge of the containment flaps and the leg elastics (the ears and front tabs can be cut off). Ensure that the absorbent core is not cut or opened up; the liner should remain fully intact. The containment flaps should remain attached to the specimen.
2. Remove the back waistband, if present.
3. Snip the containment flap elastic approximately every 25 mm (1 inch) to allow the absorbent core to lay flat.
4. Mark the center of the insult zone on the absorbent article with a single, small dot using a permanent black marker. The dot should be placed on the CD midline of the absorbent core and 5 inches from the front edge of the absorbent core.
5. Weigh the specimen and record the value to the nearest 0.001 gram.

Specimen Preparation for Absorbent Composites
1. Mark the center of the target insult zone on the absorbent composite with a single, small dot using a permanent black marker. The dot should be placed on the CD midline of the absorbent core and 5 inches from the front edge of the absorbent core.
2. Weigh the specimen and record the value to the nearest 0.001 gram.

Figure 14:
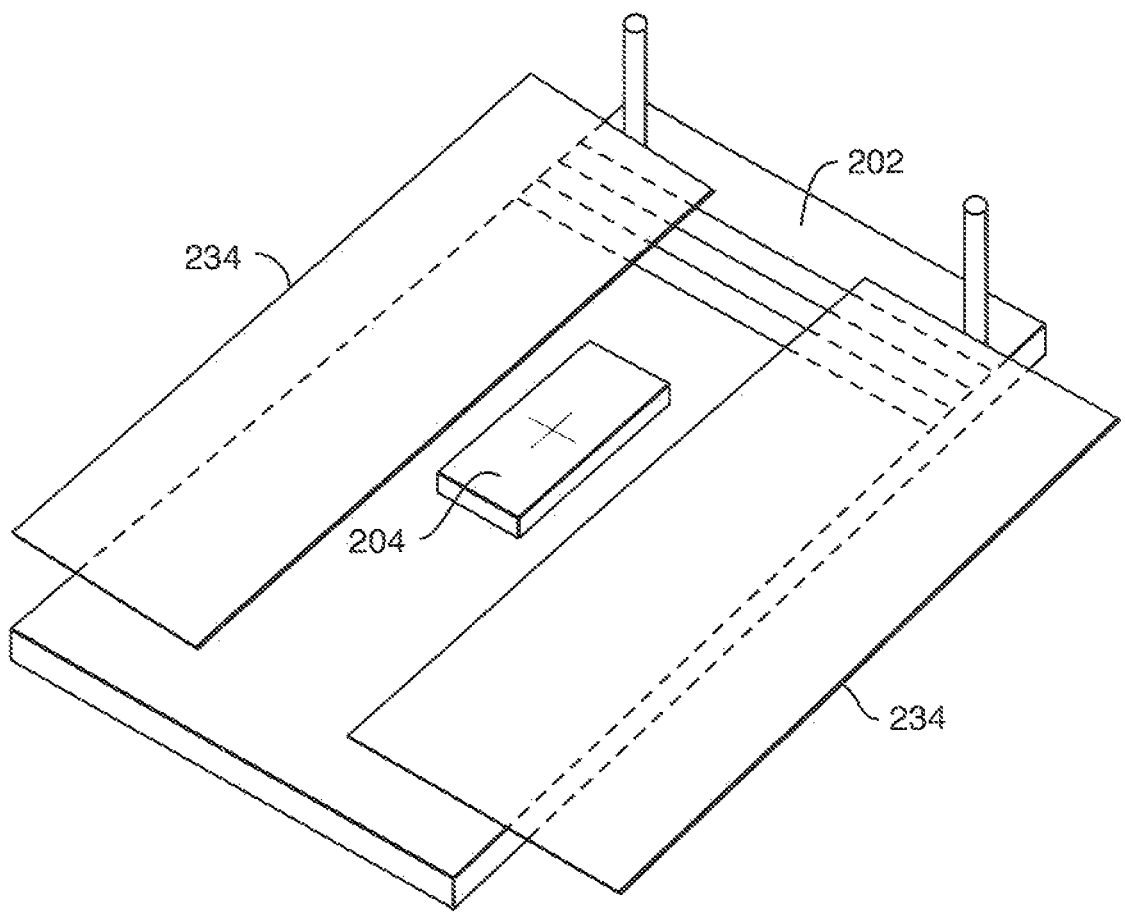
FIG. 14 is a top view of a bottom base board employed in surface moisture testing.
Figure 15:
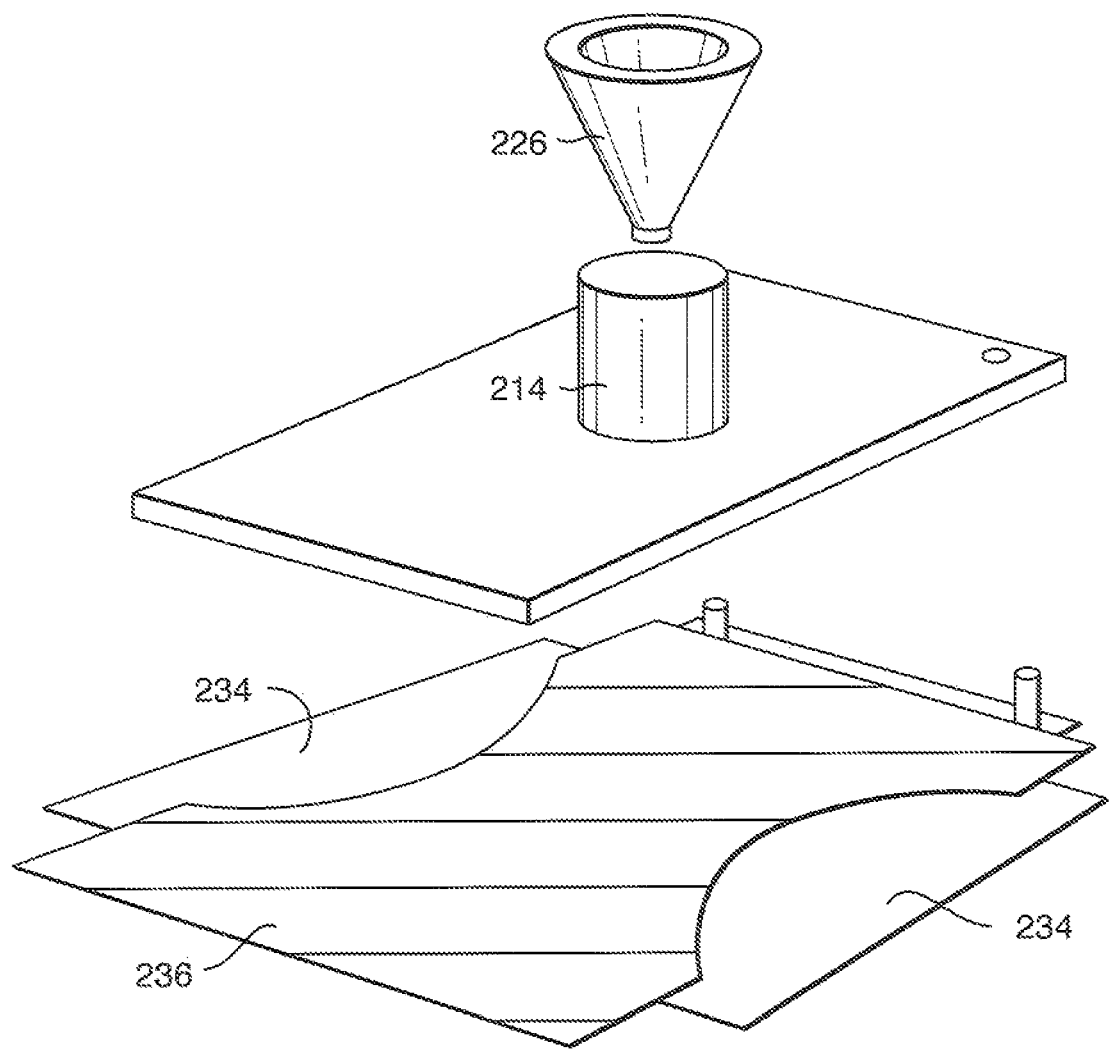
FIG. 15 is a top view of a specimen during surface moisture testing.

Testing Procedure
1. Place two pre-weighed overflow blotter papers 234 on the base member 202 of the bottom board 200, one on each side of the raised platform member 204. (See FIG. 14). Position the specimen 236, liner side up, on the bottom board 200 with the target zone centered lengthwise on the 75 by 150 mm (3 by 6 inch) raised platform. Refer to FIG. 15.
2. Place the top board 210 over the specimen 236, centering the cylindrical tube 214 over the target zone.
3. While gently pulling on the back waist of the specimen 236 to smooth out creases or wrinkles, press lightly on the top board 210 to impress the cylinder ridge into the specimen 236.
4. Place the funnel 226 into the cylindrical tube 214. The funnel 226 must be perpendicular to the specimen 236 and in the center of the cylindrical tube 214.
5. Dispense the 70 mL of testing fluid from the dispensing system directly into the funnel.
   a. The testing fluid should hit the side of the funnel 226 to avoid direct contact between the testing fluid and the specimen 236, which may cause undue pressure on the cylinder impression.
6. Start the stopwatch when the testing fluid hits the funnel 226.
7. As soon as the funnel 226 is empty, move it aside to observe the testing fluid.
8. Observe the testing fluid intake through the cylindrical tube 214 in the top plate 212 of the top board 210. Stop the stopwatch immediately when the testing fluid is not visible on the specimen 236 surface within the cylindrical tube 214.
9. Immediately set the timer for a wait time of 30 seconds and remove the top board 210.
   a. The wait time should not exceed 35 seconds.
10. Record the intake time to the nearest 0.01 second.
11. Visually check for testing fluid leakage on the overflow blotter papers 234 under the specimen 236.
    a. If the overflow blotter papers 234 are dry, they may be reused on the next specimen 236 insult.
    b. If leakage is observed, weigh the overflow blotter papers 234 to the nearest 0.001 grams and record the value.
12. After the wait time has elapsed, place a pre-weighed surface moisture dry blotter paper on the surface of the specimen 236 directly over the insult zone. Place the non-permeable, non-flexible clear board (177 grams) on top of the blotter paper, centered over the blotter paper.
13. Immediately set the timer for a wait time of 2 minutes.
14. After the 2 minute waist time has elapsed, immediately remove the non-permeable, non-flexible board and weigh the wet surface moisture blotter paper to the nearest 0.001 grams and record the value.
15. Weigh the wet specimen weight to the nearest 0.001 grams and record the value.
16. If a second insult intake time is desired, that data can be collected now by repeating steps 1-9 of this testing procedure.

Results
1. Report the dry specimen weight to the nearest 0.001 gram.
2. Report the intake time to the 0.1 second for each insult.
3. If overflow occurred, report the following:
   a. Dry blotter weight of the overflow blotters to the nearest 0.001 gram.
   b. Wet blotter weight of the overflow blotters to the nearest 0.001 gram.
   c. The amount of overflow to the nearest 0.001 gram, which can be calculated by subtracting the dry blotter weight from the wet blotter weight of the overflow blotters.
4. Report the dry blotter weight for the surface moisture blotter to the nearest 0.001 gram.
5. Report the wet blotter weight for the surface moisture blotter to the nearest 0.001 gram.
6. Report the amount of surface moisture to the nearest 0.001 grams, which can be calculated by subtracting the dry surface moisture blotter weight from the wet surface moisture blotter weight.
7. Report the amount of testing fluid actually dispensed by summing the amount of overflow in grams, the amount of surface moisture in grams, and the wet specimen weight in grams minus the dry specimen weight in grams.

Experiment 1

In this experiment, absorbent composites were made by hand and compared against each other to quantify the surface moisture of each absorbent composite.

Eight different absorbent composites were assembled by hand according to Table 2 below, utilizing the corresponding material descriptions listed in Table 1: Material Descriptions above, and ten of each absorbent composite were tested according to the Surface Moisture test method described above to determine the surface moisture of each absorbent composite.

TABLE 2

Absorbent Composites

| Absorbent Composite | Bodyside Liner | Acquisition Layer | Fluid Transfer Layer |
|---|---|---|---|
| 1 | A | H | J |
| 2 | B | H | J |
| 3 | A | C | J |
| 4 | B | C | J |
| 5 | A | H | I |
| 6 | B | H | I |
| 7 | A | C | I |
| 8 | B | C | I |

The bodyside liner of each absorbent composite was ultrasonically bonded to the acquisition layer utilizing the pattern illustrated in FIG. 7, such that the bonding pattern had 66 bonding points per square inch. The bonding pattern illustrated in FIG. 7 provides for each bonding point to have an area of about 0.98 mm². The absorbent body for each absorbent composite code was a rectangular, flat absorbent pad air formed on commercially available equipment (such as from Curt G. Joa, Inc., Sheboygan Falls, Wis. 53085) of a pulp fluff/superabsorbent material homogeneous mixture with uniform thickness, density, and basis weight on a 10 gsm spunbond-meltblown-spunbond backing sheet (Material I in Table 1: Material Descriptions above) with a pad length of 353 mm and a pad width of 90 mm. The absorbent capacity of the absorbent body was 485 g and contained 70% superabsorbent material (EVONIK SXM-9500, available from Evonik Stockhausen Inc., GmbH, Greensboro, N.C., U.S.A) and 30% pulp fluff (Weyerhaeuser 7.5% moisture CF-416 Southern Softwood Kraft fluff pulp, available from Weyerhaeuser Company, Geneva, Switzerland). The absorbent composite density was 0.25 g/cc measured under a pressure of 1.36 kPa. The absorbent composites did not have any waist or leg elastics and did not have any containment flaps.

TABLE 3

Surface Moisture.

| Absorbent Composite | Surface Moisture Level | Absorbent Composite |
|---|---|---|
| 1 | Lower Than | 3 |
| 2 | Lower Than | 4 |
| 5 | Lower Than | 7 |
| 6 | Lower Than | 8 |

Figure 16:
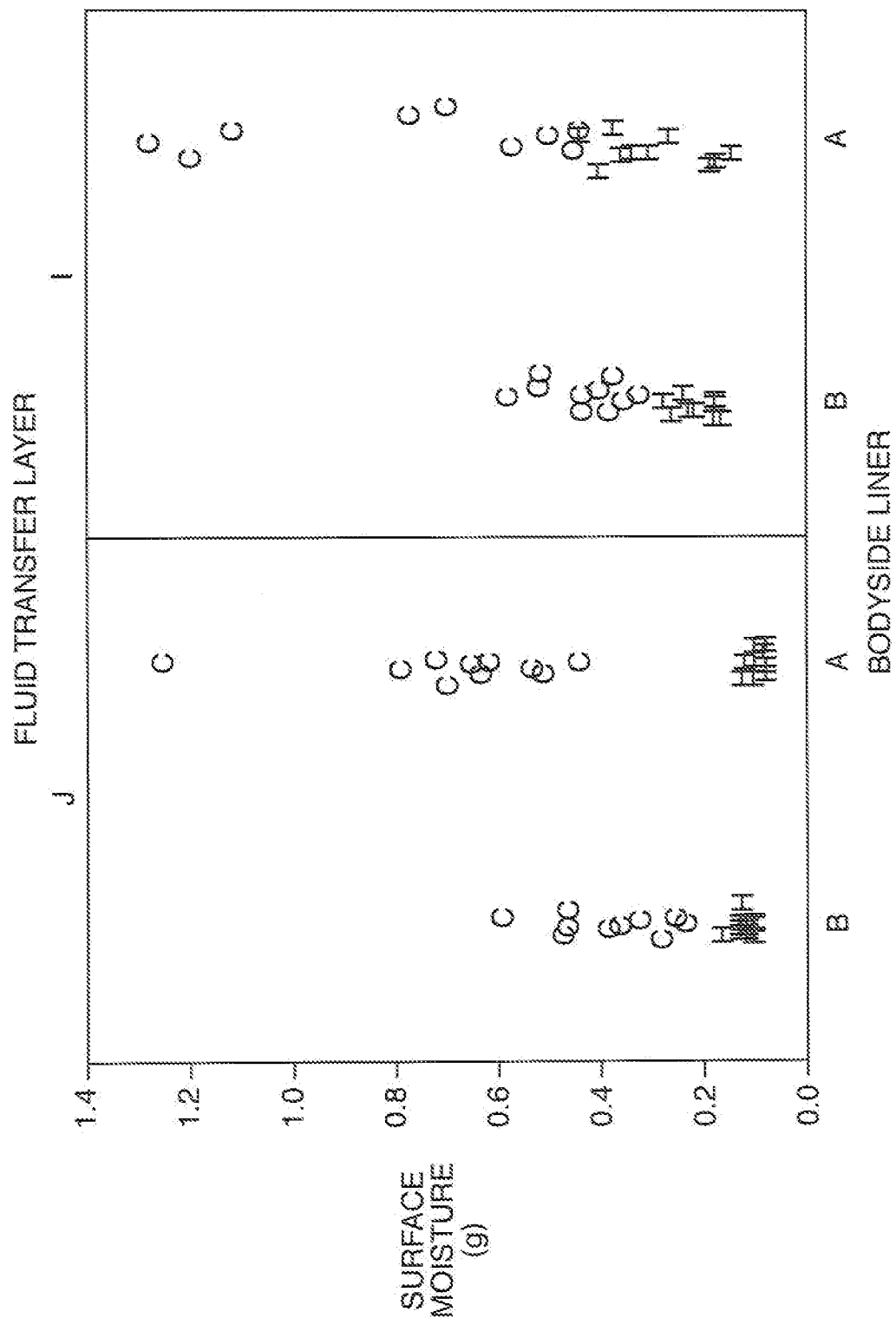
FIG. 16 is a graph depicting the results of surface moisture testing.

As illustrated in Table 3 and FIG. 16, the composition of the acquisition layer has an impact on the amount of surface moisture of an absorbent composite. As illustrated in Table 3 and FIG. 16, the absorbent composites with the acquisition layer composed of a 35 gsm through-air bonded-carded web composite composed of a homogeneous mixture of about 35% Huvis N-189 (PE/PP 6d) fibers, about 35% Huvis N-215 (PE/PP 2d) fibers and about 30% Huvis SD-10 PET 6d fibers had a lower surface moisture and lower variability than the absorbent composites that had a different acquisition layer but the same respective bodyside liner and fluid transfer layer.

Experiment 2

In this experiment, absorbent composites were made by hand and compared against each other to quantify the surface moisture of each absorbent composite relative to the method utilized to bond the bodyside liner to the acquisition layer.

Three different absorbent composites were assembled by hand according to Table 4 below, utilizing the material descriptions listed in Table 1: Material Descriptions above, and ten of each absorbent composite were tested according to the Surface Moisture test method described above to determine the surface moisture of each absorbent composite.

TABLE 4

Absorbent Composites

| Absorbent Composite | Bodyside Liner | Acquisition Layer | Fluid Transfer Layer | Bonding Method |
|---|---|---|---|---|
| 1 | A | H | J | Ultrasonic Bonding |
| 2 | A | H | J | Adhesive |
| 3 | A | H | J | No bonding |

The bodyside liner of each absorbent composite was ultrasonically bonded to the acquisition layer utilizing the pattern illustrated in FIG. 7, such that the bonding pattern had 66 bonding points per square inch. The bonding pattern illustrated in FIG. 7 provides for each bonding point to have an area of about 0.98 mm². The bodyside liner was adhesively bonded to the acquisition layer for absorbent composite code 2 with 12.5 gsm of adhesive H2525A available from Bostik Inc., U.S.A. utilizing a unibody spray nozzle with a 0.012 inch orifice diameter as available as manufacturing part No. 152168 from Nordson Corp., U.S.A. The absorbent body for each absorbent composite code was a rectangular, flat absorbent pad air formed on commercially available equipment (such as from Curt G. Joa, Inc., Sheboygan Falls, Wis. 53085) of a pulp fluff/superabsorbent material homogeneous mixture with uniform thickness, density, and basis weight on a 10 gsm spunbond-meltblown-spunbond backing sheet (Material I in Table 1: Material Descriptions above) with a pad length of 353 mm and a pad width of 90 mm. The absorbent capacity of the absorbent body was 485 g and contained 70% superabsorbent material (EVONIK SXM-9500, available from Evonik Stockhausen Inc., GmbH, Greensboro, N.C., U.S.A) and 30% pulp fluff (Weyerhaeuser 7.5% moisture CF-416 Southern Softwood Kraft fluff pulp, available from Weyerhaeuser Company, Geneva, Switzerland). The absorbent composite density was 0.25 g/cc measured under a pressure of 1.36 kPa. The absorbent composites did not have any waist or leg elastics and did not have any containment flaps.

Figure 17:
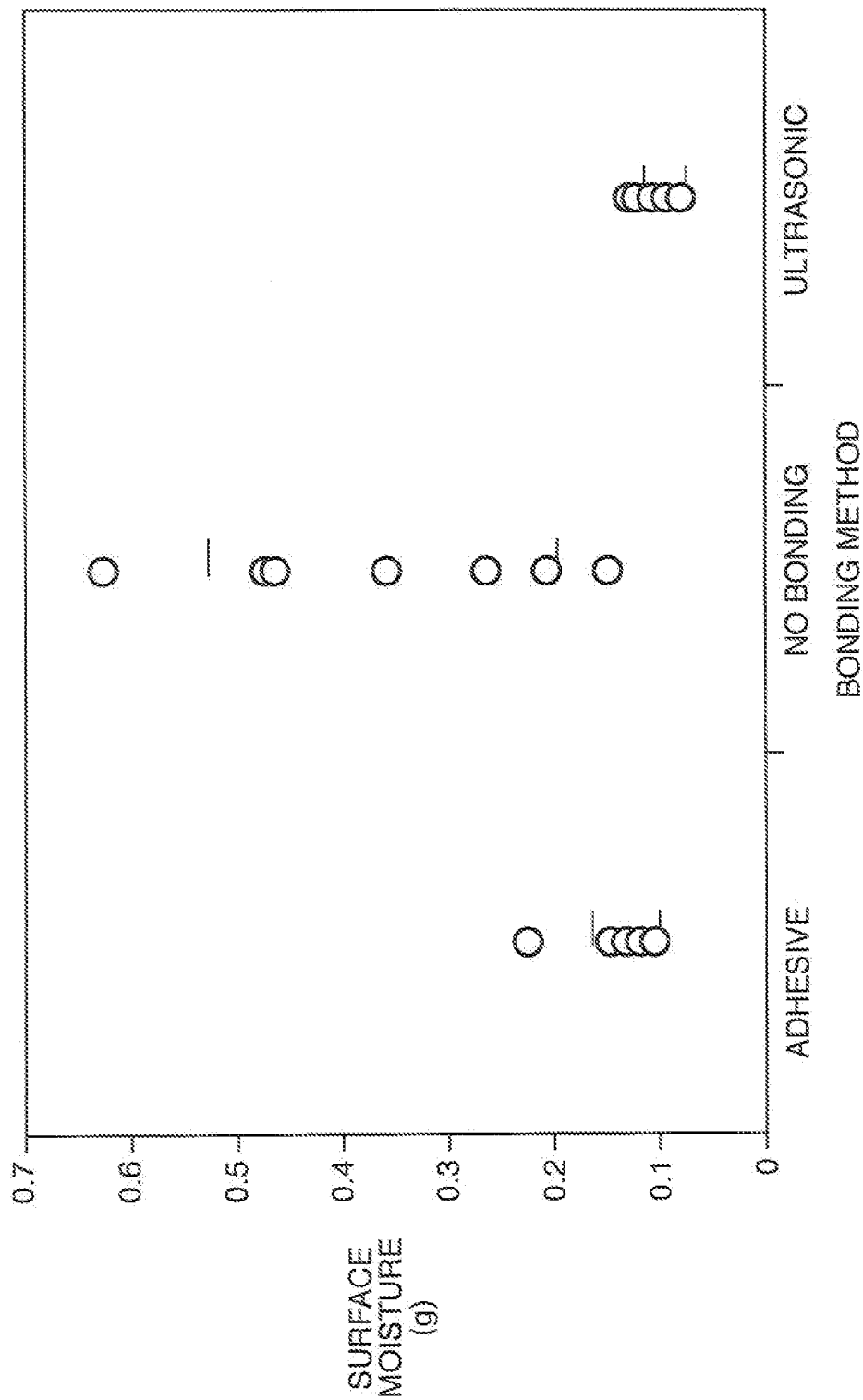
FIG. 17 is a graph depicting the results of surface moisture testing.
Figure 18:
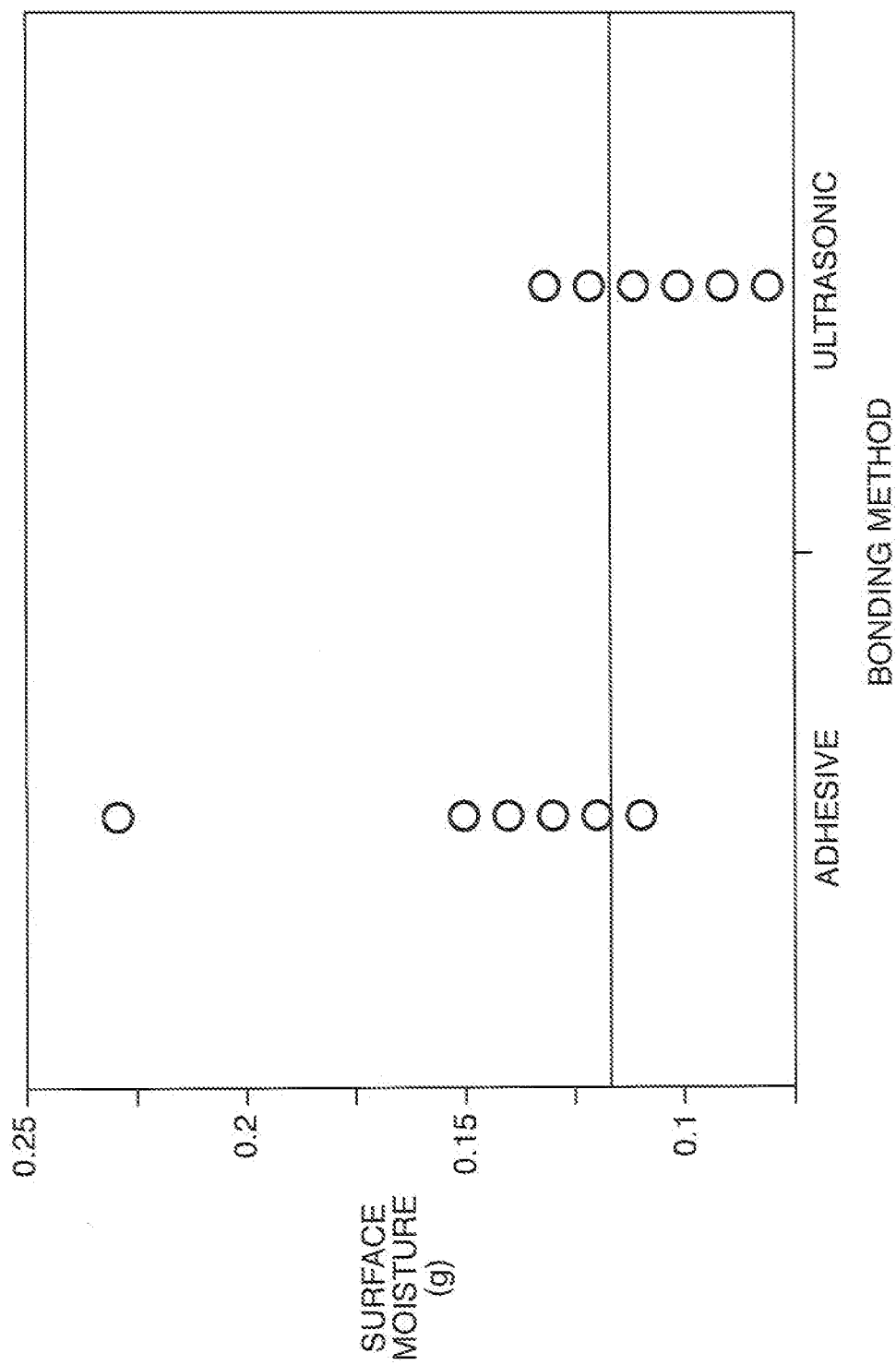
FIG. 18 is a graph depicting the results of surface moisture testing.

As can be seen in FIG. 17, attaching the bodyside liner to the acquisition layer has an impact on the surface moisture of the absorbent composite. As can be seen in FIG. 17, attaching the bodyside liner to the acquisition layer can decrease the surface moisture of the absorbent composite and can lower the variability in surface moisture. In order to detect the differences between the use of adhesive and ultrasonic bonding, FIG. 18 illustrates only the absorbent composite codes utilizing adhesive or ultrasonic bonding to bond the bodyside liner to the acquisition layer. As can be seen in FIG. 18, the use of ultrasonic bonding to bond the bodyside liner and the acquisition layer significantly reduces the surface moisture of an absorbent composite compared to adhesively bonding the bodyside liner to the acquisition layer.

Experiment 3

In this experiment, absorbent composites were made by hand and compared against each other to quantify the surface moisture of each absorbent composite relative to the type of material utilized as a fluid transfer layer.

Three different absorbent composites were assembled by hand according to Table 5 below, utilizing the material descriptions listed in Table 1: Material Descriptions above, and ten of each absorbent composite were tested according to the Surface Moisture test method described above to determine the surface moisture of each absorbent composite.

TABLE 5

Absorbent Composites.

| Absorbent Composite | Bodyside Liner | Acquisition Layer | Fluid Transfer Layer |
|---|---|---|---|
| 1 | A | H | J |
| 2 | A | H | I |
| 3 | A | H | K |

The bodyside liner of each absorbent composite was ultrasonically bonded to the acquisition layer utilizing the pattern illustrated in FIG. 7, such that the bonding pattern had 66 bonding points per square inch. The bonding pattern illustrated in FIG. 7 provides for each bonding point to have an area of about 0.98 mm$^2$. The absorbent body for each absorbent composite code was a rectangular, flat absorbent pad air formed on commercially available equipment (such as from Curt G. Joa, Inc., Sheboygan Falls, Wis. 53085) of a pulp fluff/superabsorbent material homogeneous mixture with uniform thickness, density, and basis weight on a 10 gsm spunbond-meltblown-spunbond backing sheet (Material I in Table 1: Material Descriptions above) with a pad length of 353 mm and a pad width of 90 mm. The absorbent capacity of the absorbent body was 485 g and contained 70% superabsorbent material (EVONIK SXM-9500, available from Evonik Stockhausen Inc., GmbH, Greensboro, N.C., U.S.A) and 30% pulp fluff (Weyerhaeuser 7.5% moisture CF-416 Southern Softwood Kraft fluff pulp, available from Weyerhaeuser Company, Geneva, Switzerland). The absorbent composite density was 0.25 g/cc measured under a pressure of 1.36 kPa. The absorbent composites did not have any waist or leg elastics and did not have any containment flaps.

Figure 19:
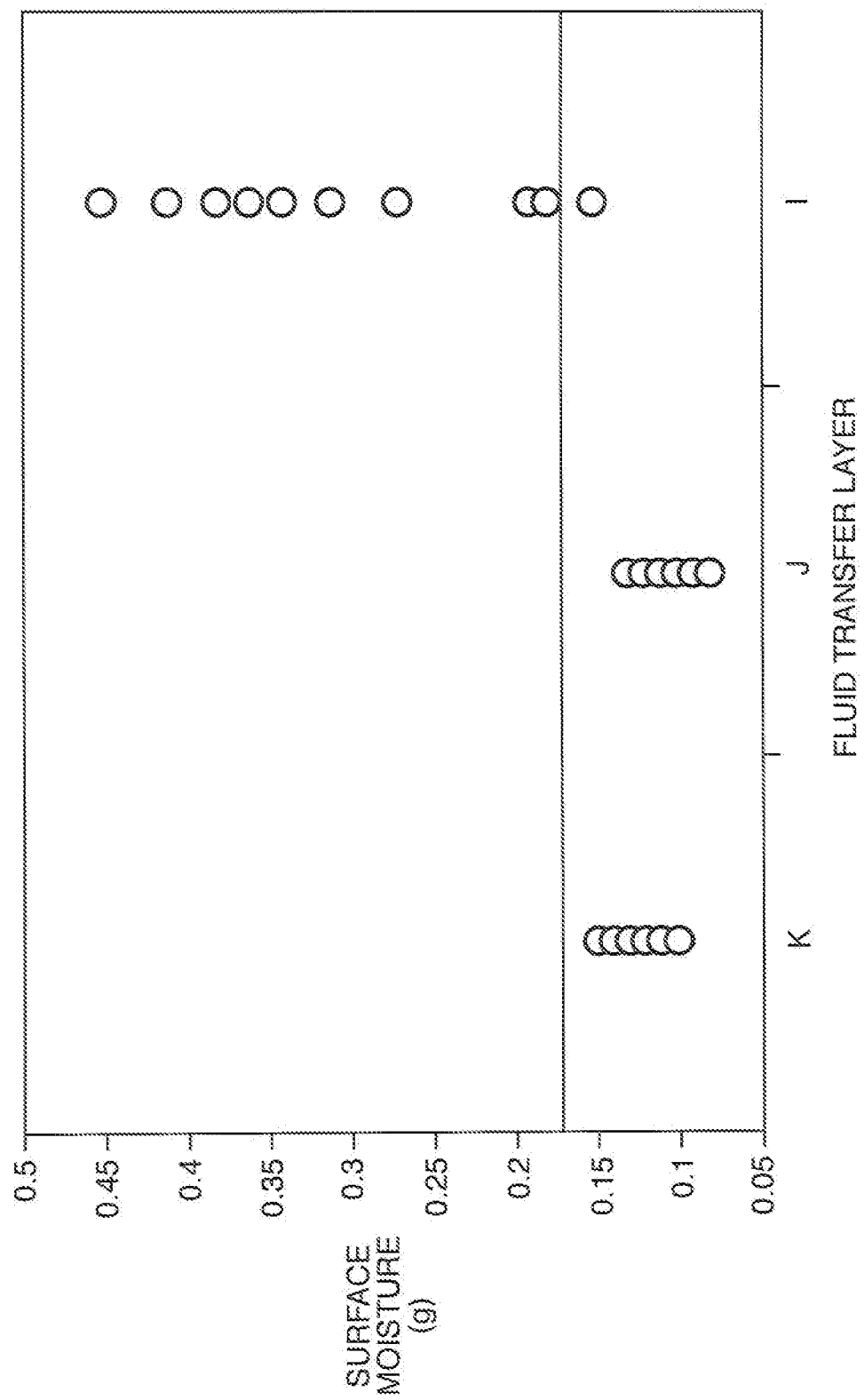
FIG. 19 is a graph depicting the results of surface moisture testing.
Figure 20:
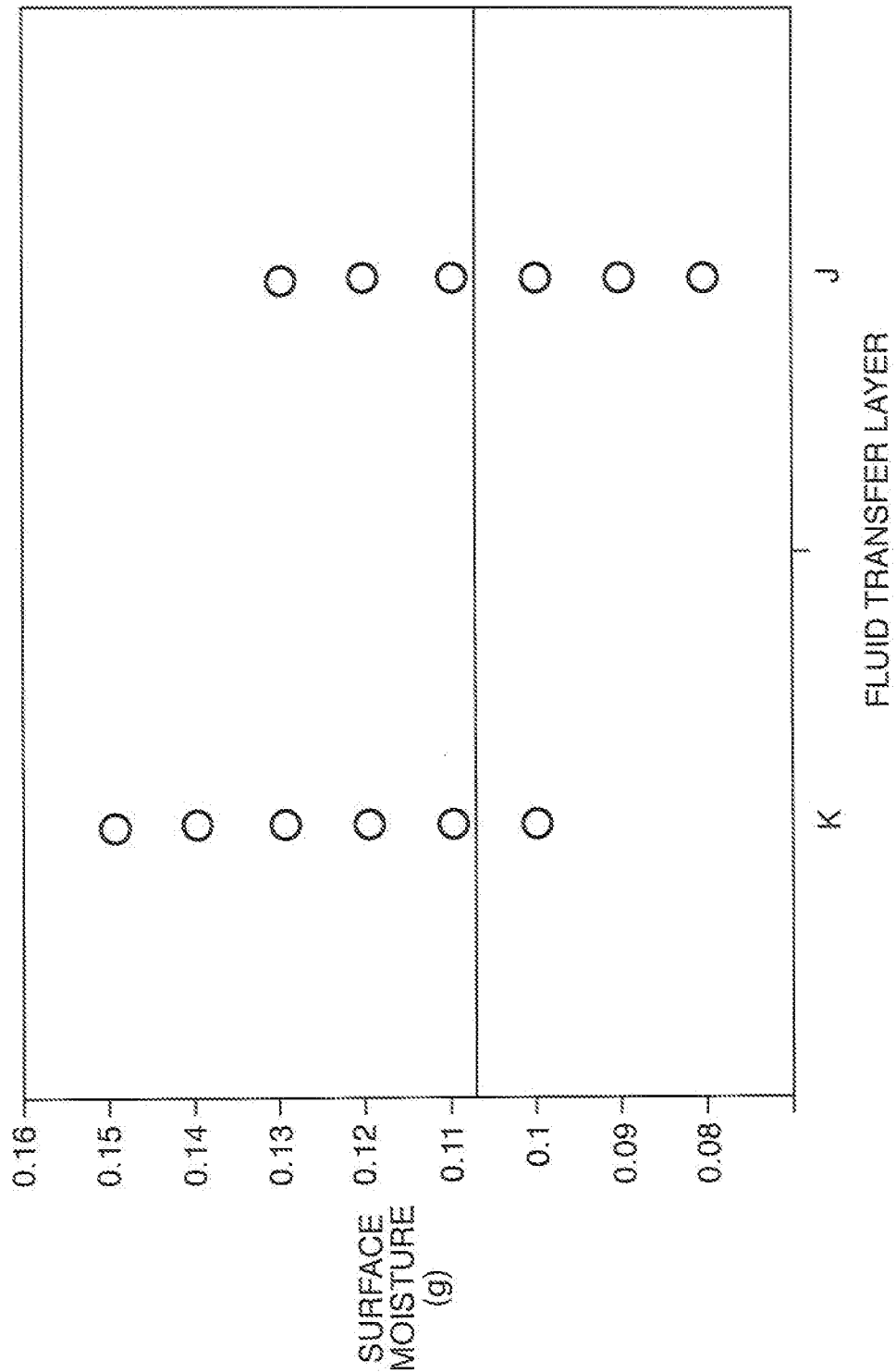
FIG. 20 is a graph depicting the results of surface moisture testing.

As can be seen in FIG. 19, the composition of the fluid acquisition layer has an impact on the surface moisture of the absorbent composite. As can be seen in FIG. 19, utilizing a fluid transfer layer composite of a 33 gsm layered spunlace material composed of an 11 gsm spunbonded polypropylene layer and a homogeneous 22 gsm hydraulically entangled (on the spunbond material) layer composed of about 48% Radiata Pine pulp and about 52% 6d polyester fibers can decrease the surface moisture of the absorbent composite and can lower the variability in surface moisture. In order to detect the differences between the use of a tissue fluid transfer layer and a hydraulically entangled fluid transfer layer, FIG. 20 illustrates only the absorbent composite codes utilizing a tissue or a hydraulically entangled fluid transfer layer. As can be seen in FIG. 20, the use of a hydraulically entangled fluid transfer layer significantly reduces the surface moisture of an absorbent composite compared to the use of a tissue fluid transfer layer.

Experiment 4

In this experiment, absorbent composites were made by hand and compared against each other to quantify the surface moisture of each absorbent composite relative to the type of material utilized as an acquisition layer.

Ten different absorbent composites were assembled by hand according to Table 6 below, utilizing the material descriptions listed in Table 1: Material Descriptions above, and ten of each absorbent composite were tested according to the Surface Moisture test method described above to determine the surface moisture of each absorbent composite.

TABLE 6

Absorbent Composites

| Absorbent Composite | Bodyside Liner | Acquisition Layer | Fluid Transfer Layer |
|---|---|---|---|
| 1 | A | H | J |
| 2 | A | E | J |
| 3 | A | F | J |
| 4 | A | G | J |
| 5 | A | A | J |
| 6 | B | H | J |
| 7 | B | E | J |
| 8 | B | F | J |
| 9 | B | G | J |
| 10 | B | A | J |

The bodyside liner of each absorbent composite was ultrasonically bonded to the acquisition layer utilizing the pattern illustrated in FIG. 7, such that the bonding pattern had 66 bonding points per square inch. The bonding pattern illustrated in FIG. 7 provides for each bonding point to have an area of about 0.98 mm$^2$. The absorbent body for each absorbent composite code was a rectangular, flat absorbent pad air formed on commercially available equipment (such as from Curt G. Joa, Inc., Sheboygan Falls, Wis. 53085) of a pulp fluff/superabsorbent material homogeneous mixture with uniform thickness, density, and basis weight on a 10 gsm spunbond-meltblown-spunbond backing sheet (Material I in Table 1: Material Descriptions above) with a pad length of 353 mm and a pad width of 90 mm. The absorbent capacity of the absorbent body was 485 g and contained 70% superabsorbent material (EVONIK SXM-9500, available from Evonik Stockhausen Inc., GmbH, Greensboro, N.C., U.S.A) and 30% pulp fluff (Weyerhaeuser 7.5% moisture CF-416 Southern Softwood Kraft fluff pulp, available from Weyerhaeuser Company, Geneva, Switzerland). The absorbent composite density was 0.25 g/cc measured under a pressure of 1.36 kPa. The absorbent composites did not have any waist or leg elastics and did not have any containment flaps.

Figure 21:
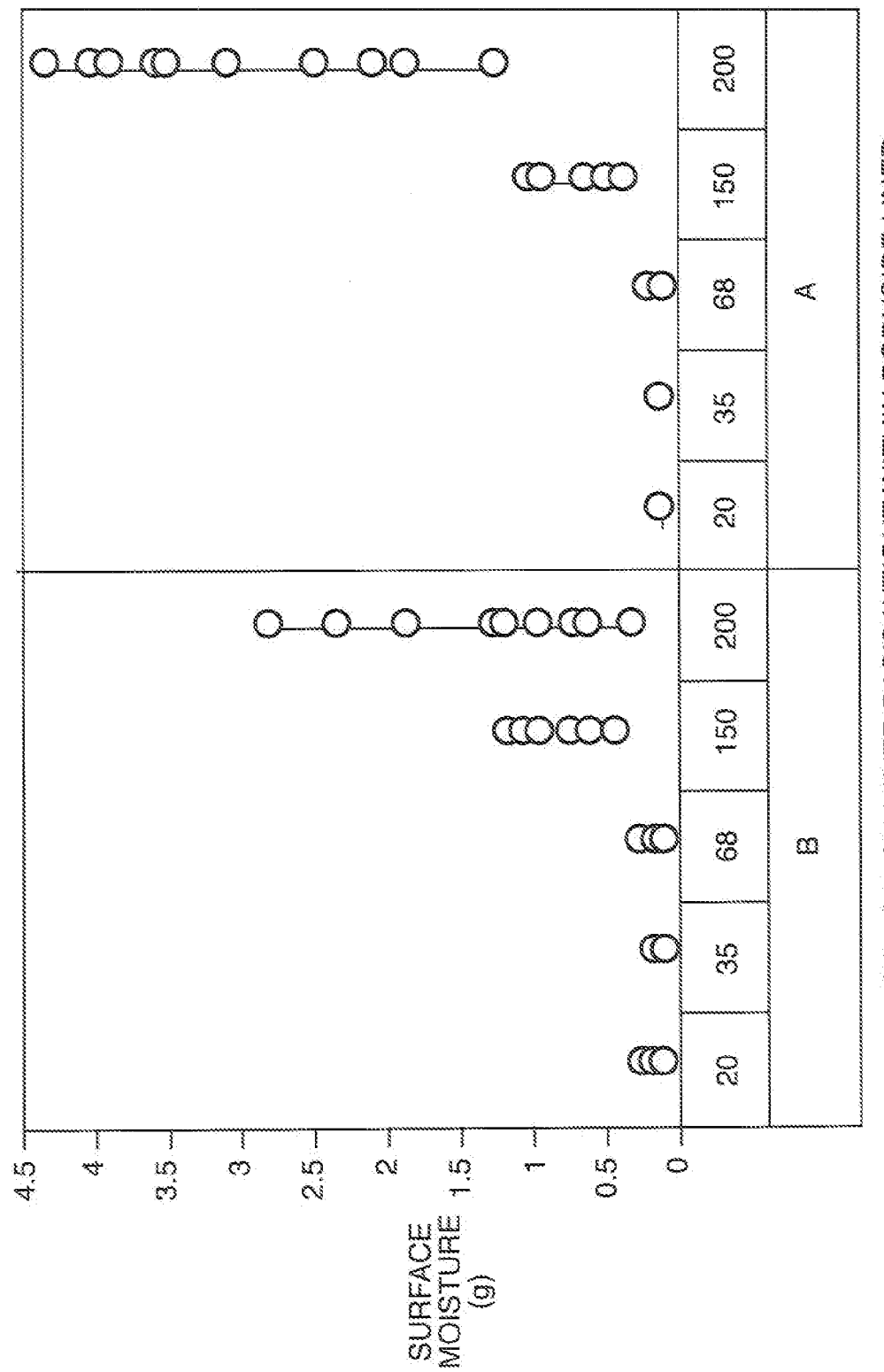
FIG. 21 is a graph depicting the results of surface moisture testing.

As can be seen in FIG. 21, the basis weight of the acquisition layer has an impact on the surface moisture of the absorbent composite. As can be seen in FIG. 21, as the basis weight of the acquisition layer increases the surface moisture of the absorbent composite increases.

Experiment 5

In this experiment, an experimental absorbent article was machine manufactured and compared against two commercially available diapers to quantify the surface moisture of each of the absorbent composites and the commercially available diapers.

An experimental absorbent article was machine manufactured utilizing standard diaper manufacturing equipment according to Table 7 below, utilizing the material descriptions listed in Table 1: Material Descriptions above, and ten of the experimental absorbent articles were tested according to the Surface Moisture test method described above to determine the surface moisture of each absorbent article and compared against ten of each of the commercially available diapers. The commercially available diapers that were used for comparison in this experiment are the Pampers® Cruisers® Size 3 purchased February 2012 and available from The Procter & Gamble Company, Cincinnati, Ohio, U.S.A. and the Huggies® Little Movers® Size 3 purchased February 2012 and available from the Kimberly-Clark Corporation, Neenah, Wis., U.S.A.

TABLE 1

| Experimental Absorbent Article | | | |
|---|---|---|---|
| Experimental Absorbent Article | Bodyside Liner | Acquisition Layer | Fluid Transfer Layer |
| 1 | A | H | J |

The bodyside liner of each experimental absorbent article machine manufactured for this experiment was ultrasonically bonded to the acquisition layer utilizing the pattern illustrated in FIG. 7, such that the bonding pattern had 66 bonding points per square inch. The bonding pattern illustrated in FIG. 7 provides for each bonding point to have an area of about 0.98 mm$^2$. The absorbent body of each experimental absorbent article was a rectangular, flat absorbent pad air formed on commercially available equipment (such as from Curt G. Joa, Inc., Sheboygan Falls, Wis. 53085) of a pulp fluff/superabsorbent material homogeneous mixture with uniform thickness, density, and basis weight on a 10 gsm spunbond-meltblown-spunbond backing sheet (Material I in Table 1: Material Descriptions above) with a pad length of 353 mm and a pad width of 90 mm. The absorbent capacity of the absorbent body was 480 g and contained 67% superabsorbent material (EVONIK SXM-9500, available from Evonik Stockhausen Inc., GmbH, Greensboro, N.C., U.S.A) and 33% pulp fluff (Golden Isles 4860 Southern Softwood Kraft fluff pulp, available from GP Cellulose LLC, Brunswick, Ga., U.S.A.). The experimental absorbent article density was 0.22 g/cc measured under a pressure of 1.36 kPa.

Figure 22:
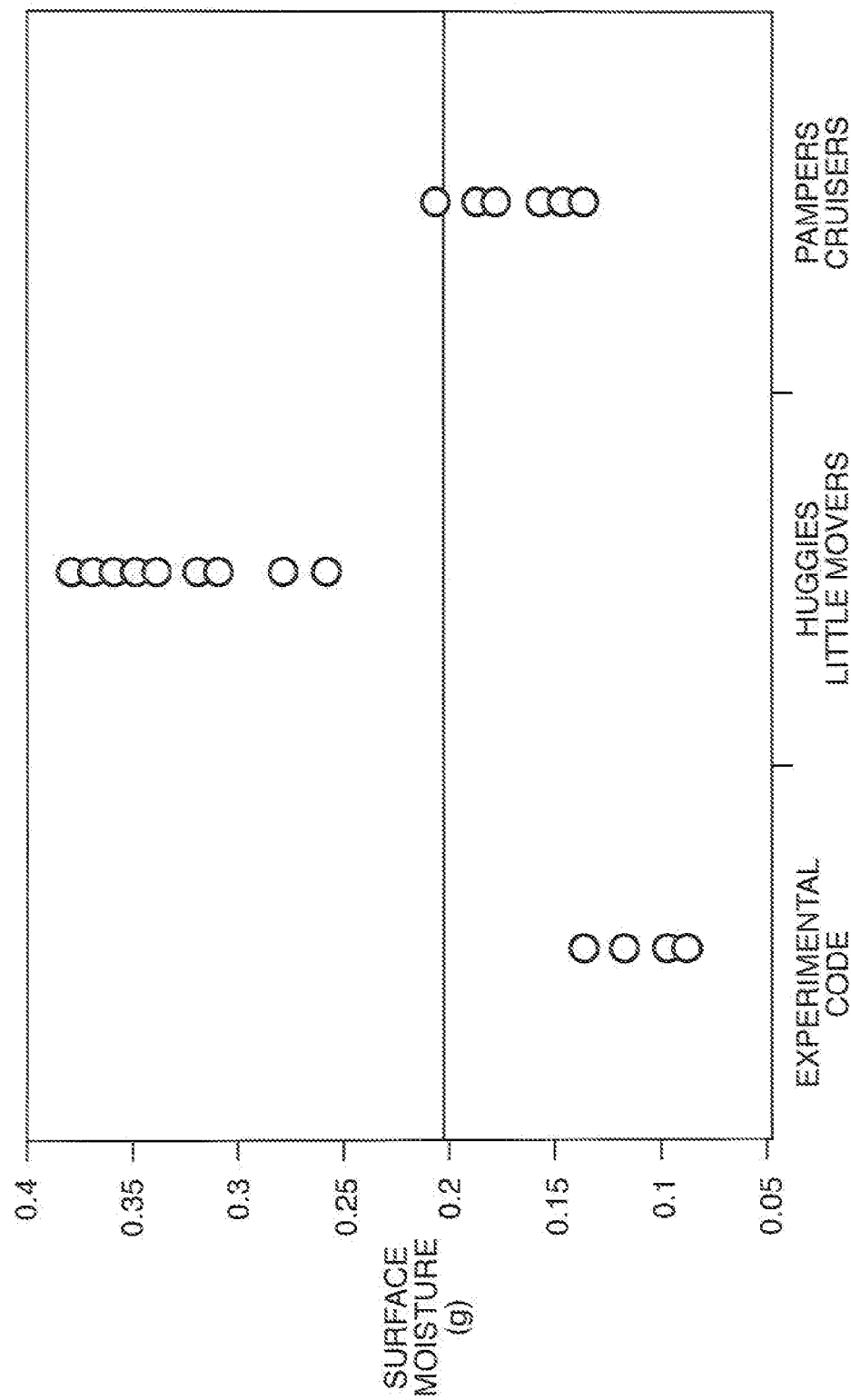
FIG. 22 is a graph depicting the results of surface moisture testing.

As can be seen in FIG. 22, the experimental absorbent article had lower surface moisture than either of the commercially available products.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. a backsheet layer;
   b. an absorbent body which is superposed on the backsheet layer, the absorbent body comprising a wearer facing surface and a garment facing surface;
   c. a fluid transfer layer bonded to the absorbent body, the fluid transfer layer comprising a first fluid transfer layer and a second fluid transfer layer, the fluid transfer layer comprising pulp fibers hydraulically entangled with polyester fibers to form the second fluid transfer layer, the fluid transfer layer at least partially encompassing the absorbent body;
   d. an acquisition layer bonded to the fluid transfer layer; and
   e. a bodyside liner point fusion bonded with the acquisition layer, the bodyside liner comprising a wearer facing layer and a garment facing layer.

2. The absorbent article of claim 1 wherein the absorbent body comprises greater than about 50% of a superabsorbent material.

3. The absorbent article of claim 1 wherein the fluid transfer layer is bonded with the acquisition layer via adhesive.

4. The absorbent article of claim 1 wherein at least one of pressure bonding, thermal bonding, and ultrasonic bonding is utilized to point fusion bond the bodyside liner to the acquisition layer.

5. The absorbent article of claim 4 wherein the point fusion bonding is ultrasonic bonding with a bond pattern providing from about 20 to about 100 bond points per square inch.

6. The absorbent article of claim 1 with a surface moisture of less than 0.6 g as tested by the Surface Moisture Test Method.

7. An absorbent article comprising:
   a. a backsheet layer;
   b. an absorbent body which is superposed on the backsheet layer, the absorbent body comprising greater than about 50% superabsorbent material;
   c. a fluid transfer layer bonded to the absorbent body, the fluid transfer layer comprising a first fluid transfer layer and a second fluid transfer layer, the fluid transfer layer comprising pulp fibers hydraulically entangled with polyester fibers to form the second fluid transfer layer, the fluid transfer layer completely encompassing the absorbent body;
   d. an acquisition layer bonded to the fluid transfer layer; and
   e. a bodyside liner point fusion bonded with the acquisition layer, the bodyside liner comprising a bonded carded web comprising a first layer and a second layer.

8. The absorbent article of claim 7 wherein one of the first and second layers of the bodyside liner further comprises fibers comprising a denier of about 1.5 and the other of the first and second layers of the bodyside liner further comprises fibers comprising a denier of about 2.

9. The absorbent article of claim 7 wherein the fluid transfer layer is bonded with the acquisition layer via adhesive.

10. The absorbent article of claim 7 wherein at least one of pressure bonding, thermal bonding, and ultrasonic bonding is utilized to point fusion bond the bodyside liner to the acquisition layer.

11. The absorbent article of claim 10 wherein the point fusion bonding is ultrasonic bonding with a bond pattern providing from about 20 to about 100 bond points per square inch.

12. The absorbent article of claim 9 with a surface moisture of less than 0.6 g as tested by the Surface Moisture Test Method.

13. An absorbent article comprising:
   a. a backsheet layer;
   b. an absorbent body which is superposed on the backsheet layer, the absorbent body comprising a wearer facing surface and a garment facing surface and comprising greater than about 50% superabsorbent material;
   c. a fluid transfer layer bonded to the wearer facing surface of the absorbent body via adhesive bonding, the fluid transfer layer comprising a first fluid transfer layer and a second fluid transfer layer, the first fluid transfer layer comprising polypropylene fibers and the second fluid transfer layer comprising pulp fibers hydraulically entangled with polyester fibers, a basis weight of the first fluid transfer layer being less than a basis weight of the second fluid transfer layer;
   d. an acquisition layer bonded to the fluid transfer layer via adhesive bonding; and
   e. a bodyside liner bonded with the acquisition layer via ultrasonic bonding, the bodyside liner comprising a wearer facing layer and a garment facing layer wherein at least one of the wearer facing and garment facing layers comprises fibers comprising a denier of about 1.5 and the other of the wearer facing and garment facing layers comprises fibers comprising a denier of about 2.

14. The absorbent article of claim 13 wherein the fluid transfer layer is further bonded with the garment facing surface of the absorbent body.

15. The absorbent article of claim 13 wherein the ultrasonic bonding has a bond pattern providing from about 20 to about 100 bond points per square inch.

16. The absorbent article of claim 13 wherein the ultrasonic bonding has a bond pattern providing from about 5% to about 30% bonded area.

17. The absorbent article of claim 13 with a surface moisture of less than 0.6 g as tested by the Surface Moisture Test Method.

18. The absorbent article of claim 1, wherein the fluid transfer layer further comprises polypropylene fibers.

19. The absorbent article of claim 18, wherein the polypropylene fibers provide the first fluid transfer layer, the first fluid transfer layer being less than about 20 gsm and the second fluid transfer layer being less than about 30 gsm.

20. The absorbent article of claim 19, wherein the second fluid transfer layer comprises greater than about 40% pulp fibers and less than about 60% polyester fibers.

21. The absorbent article of claim 7, wherein the fluid transfer layer further comprises polypropylene fibers, the polypropylene fibers providing the first fluid transfer layer.

22. The absorbent article of claim 21, wherein the first fluid transfer layer is less than about 20 gsm and the second fluid transfer layer is less than about 30 gsm.

23. The absorbent article of claim 21, wherein the second fluid transfer layer comprises greater than about 40% pulp fibers and less than about 60% polyester fibers.

24. The absorbent article of claim 13, wherein the first fluid transfer layer is less than about 20 gsm and the second fluid transfer layer is less than about 30 gsm, and wherein the second fluid transfer layer comprises greater than about 40% pulp fibers and less than about 60% polyester fibers.

\* \* \* \* \*